(12) United States Patent
Peterson

(10) Patent No.: US 7,279,555 B2
(45) Date of Patent: *Oct. 9, 2007

(54) ADVANCED ANTIGEN PRESENTATION PLATFORM

(75) Inventor: Darrell L. Peterson, Chesterfield, VA (US)

(73) Assignee: Virginia Commonwealth University, Richmond, VA (US)

( * ) Notice: Subject to any disclaimer, the term of this patent is extended or adjusted under 35 U.S.C. 154(b) by 275 days.

This patent is subject to a terminal disclaimer.

(21) Appl. No.: 10/857,733

(22) Filed: Jun. 1, 2004

(65) Prior Publication Data

US 2004/0219164 A1 Nov. 4, 2004

Related U.S. Application Data

(62) Division of application No. 09/495,947, filed on Feb. 2, 2000, now Pat. No. 6,887,464.

(60) Provisional application No. 60/118,526, filed on Feb. 2, 1999.

(51) Int. Cl.
*C07K 14/00* (2006.01)
*C12N 1/20* (2006.01)
*A61K 39/00* (2006.01)

(52) U.S. Cl. .............. 530/350; 435/235.1; 424/227.1

(58) Field of Classification Search .............. None
See application file for complete search history.

(56) References Cited

U.S. PATENT DOCUMENTS

| 4,356,270 | A | 10/1982 | Itakura |
| 4,469,863 | A | 9/1984 | Ts'o et al. |
| 4,563,423 | A | 1/1986 | Murray et al. |
| 4,882,145 | A | 11/1989 | Thornton et al. |
| 5,023,243 | A | 6/1991 | Tullis |
| 5,143,726 | A | 9/1992 | Thornton et al. |
| 5,723,335 | A | 3/1998 | Hutcherson et al. |
| 6,025,341 | A | 2/2000 | Wands et al. |
| 6,231,864 | B1 | 5/2001 | Birkett |

FOREIGN PATENT DOCUMENTS

| EP | 0 092 574 | 4/1992 |
| JP | 07-252300 | 10/1995 |
| WO | WO95/26204 | 10/1995 |
| WO | WO98/40100 | 9/1998 |
| WO | WO99/40934 | 8/1999 |

OTHER PUBLICATIONS

Yu, M. et al., A Domain of the Hepadnavirus Capsid Protein Is Specifically Required for DNA Maturation and Virus Assembly, Journal of Virology, 65(5):2511-7, 1991.*

Schlicht, H. et al., The Duck Hepatitis B Virus Core Protein Contains a Highly Phosphorylated C Terminus That Is Essential for Replication but Not for RNA Packaging, Journal of Virology, 63(7):2995-3000, 1989.*
Mason et al., 36(3) Journal of Virology 829-836 (1980).
Bodey et al., 20 Anticancer Research 2665-2676 (2000).
Dallal, MD et al., 10(2) Surgical Oncology Clinics of North America 433-447 (2001).
Beaucage et al., 22(20) Tetrahedron Letters 1859-62 (1981).
Boggs et al., 7 Antisense & Nucl. Acid Drug Devel. 461-71 (1997).
Bringas, 118 J. Structural Biol. 189-96 (1997).
Carson et al., 186(10) J. Exp. Med. 1621-22 (1997).
Cookson et al., 275 Science 41-42 (1997).
Davis et al., 160 J. Immunol. 870-76 (1998).
Gaffney et al., 29(22) Tetrahedron Letters 2619-22 (1988).
Garegg et al., 27(34) Tetrahedron Letters 4051-54 (1986).
Gilewski et al., 6 Clin. Cancer Res. 1693-1701 (2000).
Gong et al., 97(6) PNAS 2715-18 (2000).
Goodchild, 1(3) Bioconjugate Chem. 165-87 (1990).
Griffiths et al., 67(6) J. Virol. 3191-98 (1993).
Harris et al., 77 Immunol. 315-21 (1992).
Holmberg et al., 25 Bone Marrow Transplant. 1233-41 (2000).
Krieg et al., 374 Nature 546-49 (1995).
Krieg et al., 6 Antisense & Nucl. Acid Drug Devel. 133-39 (1996).
Lipford et al., 27 Eur. J. Immunol. 2340-44 (1997).
Lipford et al., 27 Eur. J. Immunol. 3420-36 (1997).
Milich, 2 Seminars in Immunol. 307-15 (1990).
Milich et al., 754 Ann. NY Acad. Sci. 187-201 (1995).
Pisetsky, 5 Immunity 303-10 (1996).
Raychaudhuri et al., 16 Nature Biotech. 1025-31 (1998).
Schirmbeck et al., 152 J. Immunol. 1110-19 (1994).
Schirmbeck et al., 155 J. Immunol. 4676-84 (1995).
Schödel et al., 66(1) J. Virol. 106-14 (1992).
Schödel et al., 268(2) J. Biol. Chem. 1332-37 (1993).
Schödel et al., 11(2) Vaccine 143-48 (1993).
Schödel et al., 11(2) Int'l Rev. Immunol. 153-65 (1994).
Schödel et al., 98 Behring Inst. Mitt. 114-19 (1997).
Simons et al., 59 Cancer Res. 5160-68 (1999).
Sparwasser et al., 27 Eur. J. Immunol. 1671-79 (1997).
Sparwasser et al., 28 Eur. J. Immunol. 2045-54 (1998).
Stacey et al., 157 J. Immunol. 2116-22 (1996).
Sun et al., 187 (7) J. Exp. Med. 1145-50 (1998).
Uhlmann et al., 90 (4) Chem. Rev. 544-84 (1990).
Wynne et al., 3 Mol. Cell. 771-80 (1999).

(Continued)

*Primary Examiner*—Bruce R. Campell
*Assistant Examiner*—Nicole E Kinsey
(74) *Attorney, Agent, or Firm*—Whitham Curtis Christofferson & Cook, P.C.

(57) ABSTRACT

The present invention provides particles for the presentation of haptens for the purpose of eliciting an immune response. The amino acid sequences of the monomers which make up the particles are derived from duck hepatitis B virus core protein. The particles may also deliver nucleic acids. The nucleic acids may be delivered for the purpose of enhancing an immune response, or for other purposes such as gene therapy.

7 Claims, 20 Drawing Sheets

OTHER PUBLICATIONS

Zimmermann et al., 160 J. Immunol. 3627-30 (1998).
Yang et al., 68(1) J. Virol 338-345 (1994).
Weizsacker et al., 24(2) Hepatol 294-299 (1996.).
Kock et al., 72(11) J. Virol 9116-20(1998).
Schödel et al., 44 J. Biotechol. 91-96 (1996).
XP-000891467 Schodel et al. "Hepatitus B Virus Core and e Antigen: Immune Recognition and Use as a Vaccine Carrier Moiety" pp. 104-110; 1996.

* cited by examiner

AMINO ACID SEQUENCE OF DUCK HEPATITIS B CORE PROTEIN

```
1                          25
MDINASRALANVYDLPDDFFPKIDDLVRDAKDALEPYWR 50                          75
SDSIKKHVLIATHFVDLIEDFWQTTQGMHEIAEALRAVI

100
PPTTTPVPAGYLIQHEEAEEIPLGDLFKHQEERIVSFQP 125                         150
DYPITARIHAHLKAYAKINEESLDRARRLLWWHYNCLLW

175
GEANVTNYISRLRTWLSTPERYRGRDAPTIEAITRPIQV 200                          225
AQGGRKTSSGTRKPRGLEPRRRKVKTTVVYGRRRSKSRD 250           262
RRAPSPQRAGSPLPRSSSSHRRSPSPRK
```

FIG. 1

NUCLEIC ACID SEQUENCE OF DUCK HEPATITIS B CORE PROTEIN

```
1                                                  50
ATGGATATCAATGCTTCTAGAGCCTTAGCCAATGTTTATGATTTGCCAGATGATTTCTTCCC

100
AAAAATTGATGATCTTGTAAGGGATGCGAAGGATGCTTTAGAACCTTATTGGAGATCAGATT

150
CAATAAAGAAACATGTTTTAATTGCAACTCACTTTGTGGATCTTATTGAAGACTTCTGGCAA

200
ACTACTCAGGGTATGCATGAAATAGCTGAAGCCTTAAGAGCAGTTATACCACCTACTACAAC 250                                                300
ACCAGTTCCCGCAGGATATCTGATTCAGCACGAAGAGGCTGAGGAGATTCCTCTGGGAGATT

350
TATTTAAACATCAGGAAGAAAGGATAGTTAGTTTCCAACCGGATTATCCTATTACTGCACGA

400
ATTCATGCACACCTGAAAGCTTATGCAAAGATTAACGAGGAATCACTGGATAGGGCTAGGAG

450
ATTGCTTTGGTGGCATTACAATTGTTTACTGTGGGGAGAAGCTAACGTTACTAATTATATTT 500                                          550
CTCGGCTTCGCACTTGGCTATCAACACCTGAGAGATACAGAGGCCGAGATGCCCCAACCATT

600
GAAGCAATCACTAGACCAATCCAAGTGGCTCAGGGAGGCAGAAAAACATCTTCGGGTACTAG

650
AAAACCTCGTGGACTCGAACCTAGAAGAAGAAAAGTTAAAACCACAGTTGTCTATGGGAGAA

700
GACGTTCAAAGTCCAGGGATAGGAGAGCCCCTTCACCCCAACGTGCGGGCTCCCCTCTCCCG 750                                  786
CGTAGTTCGAGCAGCCACAGAAGATCTCCCTCGCCTAGGAAA
```

FIG. 2

AMINO ACID SEQUENCE OF DUCK HEPATITIS B CORE PROTEIN MUTANT 1-239

```
1                         25
MDINASRALANVYDLPDDFFPKIDDLVRDAKDALEPYWR 50                          75
SDSIKKHVLIATHFVDLIEDFWQTTQGMHEIAEALRAVI

100
PPTTTPVPAGYLIQHEEAEEIPLGDLFKHQEERIVSFQP 125                         150
DYPITARIHAHLKAYAKINEESLDRARRLLWWHYNCLLW

175
GEANVTNYISRLRTWLSTPERYRGRDAPTIEAITRPIQV 200                         225
AQGGRKTSSGTRKPRGLEPRRRKVKTTVVYGRRRSKSRD

239
RRAPS
```

FIG.17

NUCLEIC ACID SEQUENCE OF DUCK HEPATITIS B CORE PROTEIN MUTANT 1-239

```
1                                                50
ATGGATATCAATGCTTCTAGAGCCTTAGCCAATGTTTATGATTTGCCAGATGATTTCTTCCC

100
AAAAATTGATGATCTTGTAAGGGATGCGAAGGATGCTTTAGAACCTTATTGGAGATCAGATT

150
CAATAAAGAAACATGTTTTAATTGCAACTCACTTTGTGGATCTTATTGAAGACTTCTGGCAA

200
ACTACTCAGGGTATGCATGAAATAGCTGAAGCCTTAAGAGCAGTTATACCACCTACTACAAC 250                                                    300
ACCAGTTCCCGCAGGATATCTGATTCAGCACGAAGAGGCTGAGGAGATTCCTCTGGGAGATT

350
TATTTAAACATCAGGAAGAAAGGATAGTTAGTTTCCAACCGGATTATCCTATTACTGCACGA

400
ATTCATGCACACCTGAAAGCTTATGCAAAGATTAACGAGGAATCACTGGATAGGGCTAGGAG

450
ATTGCTTTGGTGGCATTACAATTGTTTACTGTGGGGAGAAGCTAACGTTACTAATTATATTT 500                                                      550
CTCGGCTTCGCACTTGGCTATCAACACCTGAGAGATACAGAGGCCGAGATGCCCCAACCATT

600
GAAGCAATCACTAGACCAATCCAAGTGGCTCAGGGAGGCAGAAAAACATCTTCGGGTACTAG

650
AAAACCTCGTGGACTCGAACCTAGAAGAAGAAAAGTTAAAACCACAGTTGTCTATGGGAGAA 700            718
GACGTTCAAAGTCCAGGGATAGGAGAGCCCCTTCA
```

FIG. 18

AMINO ACID SEQUENCE OF TRUNCATED DUCK HEPATITIS B CORE PROTEIN

```
         1                         25
         MDINASRALANVYDLPDDFFPKIDDLVRDAKDALEPYWR 50                              75
         SDSIKKHVLIATHFVDLIEDFWQTTQGMHEIAEALRAVI

100
         PPTTTPVPAGYLIQHEEAEEIPLGDLFKHQEERIVSFQP 125                          150
         DYPITARIHAHLKAYAKINEESLDRARRLLWWHYNCLLW

175
         GEANVTNYISRLRTWLSTPERYRGRDAPTIEAITRPIQV 200          214
         AQGGRKTSSGTRKPRGLEP
```

FIG. 19

NUCLEIC ACID SEQUENCE OF TRUNCATED DUCK HEPATITUS B CORE PROTEIN

```
1                                                      50
ATGGATATCAATGCTTCTAGAGCCTTAGCCAATGTTTATGATTTGCCAGATGATTTCTTCCC
                                        100
AAAAATTGATGATCTTGTAAGGGATGCGAAGGATGCTTTAGAACCTTATTGGAGATCAGATT
                      150
CAATAAAGAAACATGTTTTAATTGCAACTCACTTTGTGGATCTTATTGAAGACTTCTGGCAA
         200
ACTACTCAGGGTATGCATGAAATAGCTGAAGCCTTAAGAGCAGTTATACCACCTACTACAAC
 250                                                   300
ACCAGTTCCCGCAGGATATCTGATTCAGCACGAAGAGGCTGAGGAGATTCCTCTGGGAGATT
                             350
TATTTAAACATCAGGAAGAAAGGATAGTTAGTTTCCAACCGGATTATCCTATTACTGCACGA
                   400
ATTCATGCACACCTGAAAGCTTATGCAAAGATTAACGAGGAATCACTGGATAGGGCTAGGAG
              450
ATTGCTTTGGTGGCATTACAATTGTTTACTGTGGGGAGAAGCTAACGTTACTAATTATATTT
 500                                                   550
CTCGGCTTCGCACTTGGCTATCAACACCTGAGAGATACAGAGGCCGAGATGCCCCAACCATT
                       600
GAAGCAATCACTAGACCAATCCAAGTGGCTCAGGGAGGCAGAAAAACATCTTCGGGTACTAG
             642
AAAACCTCGTGGACTCGAACCT
```

FIG. 20

SEQUENCE LISTING

<160> NUMBER OF SEQ ID NOS: 24

<210> SEQ ID NO 1
<211> LENGTH: 262
<212> TYPE: PRT
<213> ORGANISM: Duck hepatitis B virus

<400> SEQUENCE: 1

```
Met Asp Ile Asn Ala Ser Arg Ala Leu Ala Asn Val Tyr Asp Leu Pro
  1               5                  10                  15

Asp Asp Phe Phe Pro Lys Ile Asp Asp Leu Val Arg Asp Ala Lys Asp
                 20                  25                  30

Ala Leu Glu Pro Tyr Trp Arg Ser Asp Ser Ile Lys Lys His Val Leu
             35                  40                  45

Ile Ala Thr His Phe Val Asp Leu Ile Glu Asp Phe Trp Gln Thr Thr
         50                  55                  60

Gln Gly Met His Glu Ile Ala Glu Ala Leu Arg Ala Val Ile Pro Pro
 65                  70                  75                  80

Thr Thr Thr Pro Val Pro Ala Gly Tyr Leu Ile Gln His Glu Glu Ala
                 85                  90                  95

Glu Glu Ile Pro Leu Gly Asp Leu Phe Lys His Gln Glu Glu Arg Ile
            100                 105                 110

Val Ser Phe Gln Pro Asp Tyr Pro Ile Thr Ala Arg Ile His Ala His
            115                 120                 125

Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Arg Tyr Arg Gly Arg Asp Ala Pro Thr Ile Glu Ala Ile Thr Arg Pro
            180                 185                 190

Ile Gln Val Ala Gln Gly Gly Arg Lys Thr Ser Gly Thr Arg Lys
            195                 200                 205

Pro Arg Gly Leu Glu Pro Arg Arg Lys Val Lys Thr Thr Val Val
    210                 215                 220

Tyr Gly Arg Arg Arg Ser Lys Ser Arg Asp Arg Arg Ala Pro Ser Pro
225                 230                 235                 240

Gln Arg Ala Gly Ser Pro Leu Pro Arg Ser Ser Ser Ser His Arg Arg
                245                 250                 255

Ser Pro Ser Pro Arg Lys
            260
```

<210> SEQ ID NO 2
<211> LENGTH: 786
<212> TYPE: DNA
<213> ORGANISM: Duck hepatitis B virus

<400> SEQUENCE: 2

```
atggatatca atgcttctag agccttagcc aatgtttatg atttgccaga tgatttcttc      60
ccaaaaattg atgatcttgt aagggatgcg aaggatgctt tagaacctta ttggagatca     120
gattcaataa agaaacatgt tttaattgca actcactttg tggatcttat tgaagacttc     180
tggcaaacta ctcagggtat gcatgaaata gctgaagcct taagagcagt tataccacct     240
```

```
actacaacac cagttcccgc aggatatctg attcagcacg aagaggctga ggagattcct    300
ctgggagatt tatttaaaca tcaggaagaa aggatagtta gtttccaacc ggattatcct    360
attactgcac gaattcatgc acacctgaaa gcttatgcaa agattaacga ggaatcactg    420
gatagggcta ggagattgct ttggtggcat tacaattgtt tactgtgggg agaagctaac    480
gttactaatt atatttctcg gcttcgcact tggctatcaa cacctgagag atacagaggc    540
cgagatgccc caaccattga agcaatcact agaccaatcc aagtggctca gggaggcaga    600
aaaacatctt cgggtactag aaaacctcgt ggactcgaac ctagaagaag aaaagttaaa    660
accacagttg tctatgggag aagacgttca aagtccaggg ataggagagc cccttcaccc    720
caacgtgcgg gctcccctct cccgcgtagt tcgagcagcc acagaagatc tccctcgcct    780
aggaaa                                                              786
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 3
tccatgtcgc tcctgatgct                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 4
tccatgtcgt tcctgatgct                                                20

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 5
tcgtcgtttt gtcgttttgt cgtt                                           24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 6
tcgtcgttgt cgttgtcgtt                                                20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:

-continued immunostimulating oligonucleotides

<400> SEQUENCE: 7
tcgtcgtttt gtcgttttgt cgtt                                    24

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 8
tcgtcgttgt cgttttgtcg tt                                      22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 9
gcgtgcgttg tcgttgtcgt t                                       21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 10
tgtcgtttgt cgtttgtcgt t                                       21

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 11
tgtcgttgtc gttgtcgtt                                          19

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 12
tcgtcgtcgt cgtt                                               14

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      immunostimulating oligonucleotides

```
<400> SEQUENCE: 13
tcctgtcgtt ccttgtcgtt                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 14
tcctgtcgtt ttttgtcgtt                                              20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 15
tcgtcgctgt ctgcccttct t                                            21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 16
tcgtcgctgt tgtcgtttct t                                            21

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 17
tcgtcgtttt gtcgttttgt cgtt                                         24

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 18
tcgtcgttgt cgttttgtcg tt                                           22

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence:
      immunostimulating oligonucleotides
```

```
<400> SEQUENCE: 19
tgtcgttgtc gttgtcgtt                                                   19

<210> SEQ ID NO 20
<211> LENGTH: 6
<212> TYPE: DNA
<213> ORGANISM: Artificial Sequence
<220> FEATURE:
<223> OTHER INFORMATION: Description of Artificial Sequence:
      immunostimulating oligonucleotides

<400> SEQUENCE: 20 racgty                                                                  6

<210> SEQ ID NO 21
<211> LENGTH: 239
<212> TYPE: PRT
<213> ORGANISM: Duck hepatitis B virus

<400> SEQUENCE: 21
```

Met Asp Ile Asn Ala Ser Arg Ala Leu Ala Asn Val Tyr Asp Leu Pro
 1               5                  10                  15

Asp Asp Phe Phe Pro Lys Ile Asp Asp Leu Val Arg Asp Ala Lys Asp
                20                  25                  30

Ala Leu Glu Pro Tyr Trp Arg Ser Asp Ser Ile Lys Lys His Val Leu
            35                  40                  45

Ile Ala Thr His Phe Val Asp Leu Ile Glu Asp Phe Trp Gln Thr Thr
        50                  55                  60

Gln Gly Met His Glu Ile Ala Glu Ala Leu Arg Ala Val Ile Pro Pro
65                  70                  75                  80

Thr Thr Thr Pro Val Pro Ala Gly Tyr Leu Ile Gln His Glu Glu Ala
                85                  90                  95

Glu Glu Ile Pro Leu Gly Asp Leu Phe Lys His Gln Glu Glu Arg Ile
           100                 105                 110

Val Ser Phe Gln Pro Asp Tyr Pro Ile Thr Ala Arg Ile His Ala His
       115                 120                 125

Leu Lys Ala Tyr Ala Lys Ile Asn Glu Glu Ser Leu Asp Arg Ala Arg
   130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Arg Tyr Arg Gly Arg Asp Ala Pro Thr Ile Glu Ala Ile Thr Arg Pro
            180                 185                 190

Ile Gln Val Ala Gln Gly Gly Arg Lys Thr Ser Ser Gly Thr Arg Lys
        195                 200                 205

Pro Arg Gly Leu Glu Pro Arg Arg Arg Lys Val Lys Thr Thr Val Val
    210                 215                 220

Tyr Gly Arg Arg Arg Ser Lys Ser Arg Asp Arg Arg Ala Pro Ser
225                 230                 235

```
<210> SEQ ID NO 22
<211> LENGTH: 717
<212> TYPE: DNA
<213> ORGANISM: Duck hepatitis B virus

<400> SEQUENCE: 22
atggatatca atgcttctag agccttagcc aatgtttatg atttgccaga tgatttcttc     60
```

```
ccaaaaattg atgatcttgt aagggatgcg aaggatgctt tagaacctta ttggagatca    120
gattcaataa agaaacatgt tttaattgca actcactttg tggatcttat tgaagacttc    180
tggcaaacta ctcagggtat gcatgaaata gctgaagcct taagagcagt tataccacct    240
actacaacac cagttcccgc aggatatctg attcagcacg aagaggctga ggagattcct    300
ctgggagatt tatttaaaca tcaggaagaa aggatagtta gtttccaacc ggattatcct    360
attactgcac gaattcatgc acacctgaaa gcttatgcaa agattaacga ggaatcactg    420
gatagggcta ggagattgct ttggtggcat tacaattgtt tactgtgggg agaagctaac    480
gttactaatt atatttctcg gcttcgcact tggctatcaa cacctgagag atacagaggc    540
cgagatgccc caaccattga agcaatcact agaccaatcc aagtggctca gggaggcaga    600
aaaacatctt cgggtactag aaaacctcgt ggactcgaac ctagaagaag aaaagttaaa    660
accacagttg tctatgggag aagacgttca aagtccaggg ataggagagc cccttca      717

<210> SEQ ID NO 23
<211> LENGTH: 214
<212> TYPE: PRT
<213> ORGANISM: Duck hepatitis B virus

<400> SEQUENCE: 23

Met Asp Ile Asn Ala Ser Arg Ala Leu Ala Asn Val Tyr Asp Leu Pro
  1               5                  10                  15

Asp Asp Phe Phe Pro Lys Ile Asp Asp Leu Val Arg Asp Ala Lys Asp
                 20                  25                  30

Ala Leu Glu Pro Tyr Trp Arg Ser Asp Ser Ile Lys Lys His Val Leu
             35                  40                  45

Ile Ala Thr His Phe Val Asp Leu Ile Glu Asp Phe Trp Gln Thr Thr
         50                  55                  60

Gln Gly Met His Glu Ile Ala Glu Ala Leu Arg Ala Val Ile Pro Pro
 65                  70                  75                  80

Thr Thr Thr Pro Val Pro Ala Gly Tyr Leu Ile Gln His Glu Glu Ala
                 85                  90                  95

Glu Glu Ile Pro Leu Gly Asp Leu Phe Lys His Gln Glu Glu Arg Ile
            100                 105                 110

Val Ser Phe Gln Pro Asp Tyr Pro Ile Thr Ala Arg Ile His Ala His
        115                 120                 125

Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Arg Tyr Arg Gly Arg Asp Ala Pro Thr Ile Glu Ala Ile Thr Arg Pro
            180                 185                 190

Ile Gln Val Ala Gln Gly Gly Arg Lys Thr Ser Ser Gly Thr Arg Lys
        195                 200                 205

Pro Arg Gly Leu Glu Pro
    210

<210> SEQ ID NO 24
<211> LENGTH: 642
<212> TYPE: DNA
<213> ORGANISM: Duck hepatitis B virus
```

-continued

```
<400> SEQUENCE: 24
atggatatca atgcttctag agccttagcc aatgtttatg atttgccaga tgatttcttc      60
ccaaaaattg atgatcttgt aagggatgcg aaggatgctt tagaacctta ttggagatca     120
gattcaataa agaaacatgt tttaattgca actcactttg tggatcttat tgaagacttc     180
tggcaaacta ctcagggtat gcatgaaata gctgaagcct taagagcagt tataccacct     240
actacaacac cagttcccgc aggatatctg attcagcacg aagaggctga ggagattcct     300
ctgggagatt tatttaaaca tcaggaagaa aggatagtta gtttccaacc ggattatcct     360
attactgcac gaattcatgc acacctgaaa gcttatgcaa agattaacga ggaatcactg     420
gatagggcta ggagattgct ttggtggcat tacaattgtt tactgtgggg agaagctaac     480
gttactaatt atatttctcg gcttcgcact tggctatcaa cacctgagag atacagaggc     540
cgagatgccc caaccattga agcaatcact agaccaatcc aagtggctca gggaggcaga     600
aaaacatctt cgggtactag aaaacctcgt ggactcgaac ct                        642
```

ADVANCED ANTIGEN PRESENTATION PLATFORM

CROSS REFERENCE TO RELATED APPLICATIONS

The present application is a divisional and claims the benefit, under U.S.C. § 120, of U.S. patent application Ser. No. 09/495,947, filed 2 Feb. 2000, and claims the benefit, under ±U.S.C. § 119, of U.S. Provisional Application Ser. No. 60/118,526, filed 2 Feb. 1999, the contents of which are incorporated herein by reference.

BACKGROUND OF THE INVENTION

1. Field of the Invention

The invention relates to the development of vaccines and specifically to the development of an improved method for antigen presentation. The invention further relates to the delivery of nucleic acids to cells via a particle.

2. Background Description

The aim of all vaccinations is to induce specific immunity that prevents microbial invasion, eliminates microbes that have already invaded the host, or neutralizes microbial toxins. Unfortunately, the development of effective protein subunit or peptide vaccines against intracellular pathogens has been hindered by major technological and conceptual inadequacies.

One such inadequacy is the inability to elicit a strong TH1 immune response. The response of the immune system to an antigen during vaccination can be somewhat variable depending on the size and composition of the disease specific antigen, and the particular adjuvant used to enhance the immune response. Potential responses include TH1, TH2 or mixed (TH1/TH2) responses.

Cytokine profiles determine T cell regulatory and effector functions in immune responses. Cytokines play a role in directing the T cell response. Helper (CD4+) T cells orchestrate the immune response of mammals through production of soluble factors that act on other immune system cells, including other T cells. Most mature CD4+ T helper cells express one of two cytokine profiles: TH1 or TH2. TH1 cells secrete IL-2, IL-3, IFN-γ, TNF-β, GM-CSF and high levels of TNF-α. TH2 cells express IL-3, IL-4, IL-5, IL-6, IL-9, IL-10, IL-13, GM-CSF and low levels of TNF-α. The TH1 subset promotes delayed-type hypersensitivity, cell-mediated immunity, and immunoglobulin class switching to IgG2. The TH2 subset induces humoral immunity by activating B cells, promoting antibody production, and inducing class switching to IgG, and IgE.

Several factors have been shown to influence commitment to TH1 or TH2 profiles. The best characterized regulators are cytokines. IL-12 and IFN-γ are positive TH1 and negative TH2 regulators. IL-12 promotes IFN-γ production, and IFN-γ provides positive feedback for IL-12. IL-4 and IL-10 appear to be required for the establishment of the TH2 cytokine profile and to down-regulate TH1 cytokine production; the effects of IL-4 are in some cases dominant over those of IL-12. IL-13 was shown to inhibit expression of inflammatory cytokines, including IL-12 and TNF-α by LPS-induced monocytes in a way similar to IL-4. The IL-12 p40 homodimer binds to the IL-12 receptor and antagonizes IL-12 biological activity; thus it blocks the pro-TH1 effects of IL-12.

A TH1 response is marked by mobilization of macrophages, B-cells antibody producing cells, professional antigen presenting cells (APCs), and cytotoxic T lymphocytes (CTL) for the phagocytic elimination of microbes. Further, a TH1 response induces the expression of IFN-γ. IFN-γ promotes the switching of B cells to isotypes such as IgG2 which fixes complement and promotes phagocytosis by macrophages. IFN-γ also activates the antimicrobial functions of macrophages. A TH1 immune response thus induces phagocyte-dependent host reactions that are important for the elimination of intracellular microbes, and it is therefore highly desirable for a vaccine to elicit a strong TH1 response.

Several studies have reported that the cytokine IL-12 plays a critical role in inducing antiviral effects in vivo by promoting the TH1-type immune response. IL-12 is mainly produced by activated antigen presenting cells (APCs) including macrophages, dendritic cells, and B cells, and is reported to augment antibody, $CD4^+$, and CTL responses. IL-12 induces the maturation of type-1 TH cells into IFN-γ producing cells, promotes natural killer (NK) activity, and enhances CTL maturation. It is a heterodynamic cytokine consisting of two subunits, p35 and p40. The p35 subunit is constituitively expressed, while the p40 subunit is expressed only upon APC activation. It is therefore highly desirable for a vaccine to elicit the production of IL-12.

Protein subunit or peptide vaccines are often not immunologically active by themselves and must be administered with an adjuvant. Aluminum hydroxide (alum) is currently the only adjuvant approved for human use. An important disadvantage of alum is that it induces a TH2-rather than a TH1-type immune response, and this may interfere with induction of CTL. Indeed, in mice immunized with recombinant Hepatitis B surface antigen (HBsAg), the addition of alum selectively blocked activation of CD8+CTL (Schirmbeck et al., 1994). Although not essential for protective immunity against HBV, CTL may nevertheless play an important role.

The use of alum has been linked to TH2-type diseases. The much higher prevalence of asthma (a TH2-type disease) in more highly developed nations may be linked to the high hygiene level and rapid treatment of childhood infections (Cookson and Moffatt, 1997). Early exposure to bacterial DNA pushes the immune system away from TH2- and towards a TH1-type response and this may account for the lower incidence of asthma in less developed countries, where there is a much higher frequency of upper respiratory infections during childhood. It would be an advantage to have available pediatric vaccines capable of re-establishing a TH1-type response, thereby reducing the incidence of asthma.

In order to elicit a strong TH1 response by an antigen which is deposited in the extracellular fluid (which is the case with most vaccines) very high concentrations of the antigen are necessary. This cannot be accomplished in a safe and efficacious manner. However, one solution to the problem is to deliver disease-specific antigens on the surface of a particle. Both macrophages and dendritic cells internalize particles into large vacuoles where exogenous antigens can be transferred to both the class I and class II presentation pathways. This exogenous class I presentation pathway is of considerable interest for vaccine development because it provides a means of eliciting CTL immunity with antigens that are deposited into the extracellular fluid. It has been demonstrated that when exogenous antigens are particulate in nature, they are presented 1,000 to 10,000-fold more efficiently than soluble antigens in both the class I and class II pathways (Harris et al., 1992: Griffiths et al., 1993; Schodel et al., 1994; Schirmbeck et al, 1995; and Raychaudhuri and Rock, 1998). One example of the use of particles to carry antigens is that of the human hepatitis B viral core antigen (HBcAg). It has been shown that human HBcAg is capable of serving as an effective carrier for foreign epitopes which have been chemically coupled to, or genetically engineered into, the protein sequence at several selected sites (Milich, 1990; Schodel et al., 1992; Schodel et al., 1993; Schodel et al., 1994; Milich et al., 1995). Also, see, for example, the following U.S. Pat. Nos. 4,882,145; 4,882, 145, and 5,143,726, to Thornton et al. which are incorporated herein by reference. The patents are directed toward the use of fusion proteins comprised of T cell stimulating regions of the human Hepatitis B viral (HBV) nucleocapsid protein linked to a polypeptide immunogen. However, one serious drawback to the use of human HBcAg as a vaccine carrier is that antibodies against HBcAg itself (anti-HBc) also develop in recipients of the vaccine. This is a problem because the detection of HBV infection in humans, and in blood which has been donated for use in transfusions, is by screening for anti-HBc in the blood. Therefore, widespread use of a vaccine based on human HBcAg would compromise the currently used hepatitis B screening system. The use of hepatitis B-based particles from some other species (e.g. woodchuck) would also pose the same problem since they are crossreactive with human HBcAg. It is estimated that approximately 500 million people are infected with HBV worldwide. In these individuals, the administration of a vaccine based on human HBcAg would be fruitless, since their immune system would likely attack and destroy the vaccine particles before they could exert their immunizing effect. It would therefore be advantageous to have available a particulate vaccine carrier which did not interfere with current HBV screening protocols.

Another major inadequacy of current vaccines is the inability to produce vehicles to deliver haptens that are effective in stimulating a specific immune response to "quasispecies" of the invading microbe. Quasispecies are progeny of the original microbe that develop during infection. The genetic structure of quasispecies has been altered by mutation, allowing these structurally similar microbes to escape elimination by the immune system and maintain the pathological condition. It would thus also be highly desirable to develop a hapten vehicle for use in vaccines that was capable of eliciting a protective response against a wide variety of structurally similar haptens such as those exhibited by genetically hypervariable microbes (e.g. viruses). Such a hapten vehicle could stimulate an immune response against the targeted microbe and quasispecies produced during infection.

SUMMARY OF THE INVENTION

The present invention provides a composition comprised of a plurality of nucleocapsid protein monomers, the primary sequences of which are derived from duck hepatitis B virus, wherein said plurality of monomers are assembled to form a particle. The monomers may further include a first and second hapten, as well as multiple haptens, depending on the use of the particle. The particles may further include nucleic acids. Those nucleic acids may have but are not limited to sequences corresponding to SEQ IDs number 3-19.

The haptens may be associated with a disease condition caused by an agent selected from the group consisting of: single single stranded DNA viruses, double stranded DNA viruses, single stranded RNA viruses, double stranded RNA viruses, intracellular parasites, fungi, bacteria, and cancer.

The invention further comprises a method of delivering nucleic acids to a subject in need thereof by administering a composition comprised of a plurality of nucleocapsid protein monomers assembled in the form of a particle where the particle incorporates the desired nucleic acid sequence.

The present invention also provides a method for making particles, which method comprises the steps of: providing a composition comprised of a plurality of nucleocapsid protein monomers, the primary sequences of which are derived from duck hepatitis B virus, wherein said plurality of monomers are assembled to form a particle, exposing said particle to a charged agent to disassemble the particle and allow for mixing in nucleic acids or other nucleocapsid monomers that include different haptens, and removing said charged agent; the removal of the charged agent allows the monomers to reassemble. Further steps may be included in the method, such as removing unwanted nucleic acids and adding desired nucleic acids. The charged agent may be a divalent cation selected from the group consisting of: $Mg^{+2}$, $Zn^{+2}$, $Ba^{+2}$, $Sr^{+2}$, $Ca^{+2}$ and $Pb^{+2}$.

BRIEF DESCRIPTION OF THE DRAWINGS

FIG. 1. Amino acid sequence of duck HBcAg (SEQ ID NO: 1).

FIG. 2. Nucleic acid sequence of duck HBcAg (SEQ ID NO: 2).

FIG. 17. Amino acid sequence of duck HBcAg (1-239) (SEQ ID NO: 2).

FIG. 18. Nucleic acid sequence of duck HBcAg (1-239) (SEQ ID NO: 22).

FIG. 19. Amino acid sequence of t-duck HBcAg (SEQ ID NO: 23).

FIG. 20. Nucleic acid sequence of t-duck HBcAg (SEQ ID NO: 24).

DETAILED DESCRIPTION OF THE PREFERRED EMBODIMENTS OF THE INVENTION

Figure 3:
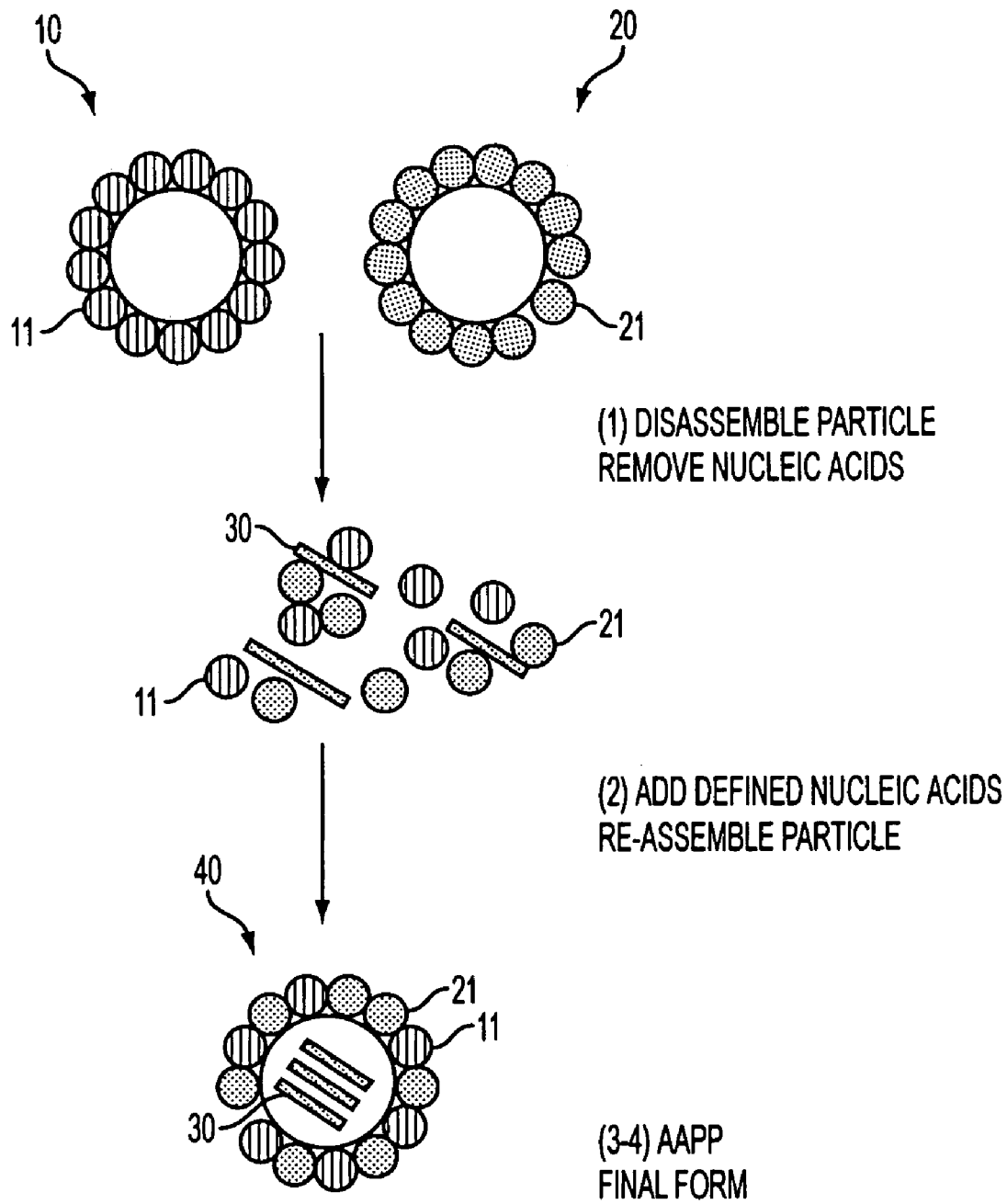
FIG. 3. Illustration of extrinsic mosaic recombinant duck HBcAg particles.

Definitions:

Antibody: a molecule that is a member of a family of glycosylated proteins called immunoglobulins (e.g. IgG, IgE, etc.), which can specifically combine with an antigen.

Antigen: term used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility.

Antigenic determinant: the actual structural portion of the antigen that is immunologically bound by an antibody combining site or T cell receptor. The term is interchangeable with "epitope".

Cytokine: Protein hormones which promote cell proliferation and differentiation. Cytokines are secreted by immune cells (T-cells, B-cells, macrophages, dendritic cells, etc.) in response to antigenic stimulation.

GM-CSF: Granulocyte-monocyte colony stimulating factor is a cytokine that generally acts on bone marrow to increase the production of inflammatory leukocytes. It also is a macrophage-activating factor and promotes the differentiation of Langerhans cells into dendritic cells.

Hapten: a disease specific antigenic determinant identified by biochemical, genetic or computational means.

HBcAg: T cell stimulating proteins or polypeptides having an amino acid residue sequence that corresponds to an amino acid residue sequence encoded by the hepatitis B virus nucleocapsid protein gene.

IFN-γ: Interferon-γ is produced by activated CD4+ and CD8+ T cells and by NK cells. Production of IFN-γ is a direct consequence of antigen activation and is enhanced by the presence of the cytokines IL-2 and IL-12.

Monocytic cells: A monocytic cell is released from bone marrow as an incompletely differentiated cell and is referred to as a "monocyte".

Nucleic acid (or oligonucleotide): polymeric form of nucleotides at least five bases in length. The nucleotides may be deoxyribonucleotides, ribonucleotides, or modified forms of either. They may be double- or single-stranded.

Polypeptide or peptide: a linear series of amino acids connected to each other by peptide bonds between the alpha-amino and carboxy groups of adjacent amino acids. They can be a variety of lengths, whether in their neutral (uncharged) forms, or forms which are salts, and whether free of or containing modifications such as glycosylation, side chain oxidation phosphorylation and the like. Also included are proteins modified by additional substituents such as glycosyl units, lipids, or inorganic ions such as phosphates, as well as modifications relating to chemical conversions or the chains, such as oxidation of sulfhydryl groups.

Protein: a polypeptide having about 70 or more amino acids.

TH (as in TH1 and TH2): T helper cells. Naive CD4+ cells can differentiate into the subsets TH1 and TH2. This differentiation is influenced by the cytokine environment produced early in response to a microbe that triggers an immune response. The principal effector function of TH1 cells is the phagocyte-mediated defense against infection. TH2 cells are primarily involved in the development of an antibody and allergenic immune response.

The instant invention provides a new type of vehicle for use in the presentation of haptens for the purpose of eliciting an immune response, and for the delivery of nucleic acids for use in enhancing an immune response, for gene therapy, and for other uses. The vehicle is a particle, the structure of which is based in part on the duck hepatitis B viral core antigen (duck HBcAg). Applicants have discovered that particles formed by assembling recombinant forms of duck HBcAg are highly immunogenic, eliciting a TH1 type immune response and that the particles can be disassembled and reassembled under relatively mild, non-denaturing conditions. This latter finding, coupled with known recombinant DNA techniques, opens the prospect of generating particles which carry a wide variety of different haptens on a single particle. Further, the reversible disassembly process provides a means to generate particles that contain nucleic acids which may be immune stimulating (in order to further enhance the immune response), or which may be useful for some other purpose (e.g. for genetic therapy).

Native duck HBcAg particles are 32-34 nm particle composed of 240 identical subunit monomers and are very similar in structure to those of human HBcAg. However, Applicants have found that duck HBcAg is not cross-reactive with woodchuck or human HBcAg antibodies. This is an important finding for two reasons: firstly, the use of duck HBcAg particles as hapten carriers would not interfere with current protocols for detecting human HBcAg since no anti-human HBcAg antibodies would be generated. Secondly, individuals which already have anti-human HBcAg antibodies would still be able to be immunized with the duck HBcAg. This discovery therefore represents a significant advance in the development of particulate vaccine vehicles.

In preferred embodiments of the present invention, the primary amino acid sequences of the monomers which make up the particles of the present invention, and the nucleic acid sequences which encode them, are "derived from" duck HBcAg. Duck HBcAg monomers consist of 262 amino acids (shown in FIG. 1, SEQ ID #1), with an assembly domain comprised of residues 1-200 and an arginine rich nucleic acid binding domain consisting of residues 201-262. By "derived from" we mean that the present invention encompasses particles composed of recombinant monomers whose sequences are identical to those of native duck HbcAg, and also of recombinant monomers with variations in both the amino acid and/or the nucleic acid sequences of duck HBcAg. For example, alternative cloning sites may be genetically engineered into the nucleic acid sequence for the purpose of moving the sequence into a vector, inserting haptens, amino acids substitutions may be made, etc. Any genetic engineering possibility known to those of skill in the art may be applied so long as the resulting monomers still retain the ability to function in the practice of the present invention. In particular, the duck hepatitis B core protein shown in FIG. 1 is able to assemble into a particle as shown in FIG. 3. The protein and nucleic acid sequences corresponding to duck HBcAg may be modified by deletions, insertions, or substitutions as necessary in order to carry out or to optimize the practice of the present invention, and all such modifications are intended to be within the scope of the present invention. A modified protein derived from duck hepatitis B core protein could include one or more haptens inserted into SEQ ID #1 (or the truncated versions shown in FIGS. 17 and 19, or other truncated versions) and would have the ability to assemble into a particle as shown in FIG. 3. The methods for carrying out such genetic modifications are well known to those of skill in the art.

In a preferred embodiment of the present invention the monomer sequences are derived from a recombinant form of duck HBcAg known as BC-201D, the amino acid sequence of which is given in FIG. 1 (SEQ ID #1). The nucleic acid sequence which encodes BC-201D is given in FIG. 2 (SEQ ID #2). The correspondence between the single letter code and the amino acids or nucleic acid bases are given in Table 1.

TABLE 1

Table of Correspondence Between Single Letter Code and Amino Acid or Nucleotide Base

| SYMBOL | |
|---|---|
| | AMINO ACID |
| Y | L-tyrosine |
| G | glycine |
| F | L-phenylalanine |
| M | L-methionine |
| A | L-alanine |

TABLE 1-continued

Table of Correspondence Between Single Letter Code and Amino Acid or Nucleotide Base

| SYMBOL | |
|---|---|
| S | L-serine |
| I | L-isoleucine |
| L | L-leucine |
| T | L-threonine |
| V | L-valine |
| P | L-proline |
| K | L-lysine |
| H | L-histidine |
| Q | L-glutamine |
| E | L-glutamic acid |
| Z | L-glutamic acid or L-glutamine |
| W | L-tryptophan |
| R | L-arginine |
| D | L-aspartic acid |
| N | L-asparagine |
| B | L-aspartic acid or L-asparagine |
| C | L-cysteine |
| | NUCLEOTIDE BASE |
| A | adenine |
| C | cytosine |
| G | guanine |
| T | thymine |

Recombinant duck HBcAg when made in, for example, *Escherichia coli* spontaneously self-assembles into macromolecular core particles. With respect to obtaining particles for use in the practice of the present invention, the means of generating appropriate quantities of particles and purifying them are well known to those of skill in the art. See, for example, U.S. Pat. No. 4,356,270 to Itskura and U.S. Pat. No. 4,563,423 to Murray et al., whose disclosures are incorporated herein by reference.

In a preferred embodiment of the present invention, the particles of the present invention are produced in an *E. coli* recombinant system. However, the particles may be produced by expression of the monomers in a variety of other recombinant expression systems. For example, yeast, insect cells (using for example, a baculovirus expression vector), plant cells (e.g. tobacco, potato, corn, etc.), transgenic animals, or mammalian cell culture systems. Any appropriate expression system that correctly produces the particles of the present invention may be used in the practice of the present invention. Such systems and their use for the production of recombinant proteins are well known to those of skill in the art.

In a preferred embodiment of the present invention, the particles will be comprised of monomers which have been genetically engineered to contain one or more foreign (i.e. non-duck) haptens. The haptens will be carried by the particle into the host upon vaccination and thus presented to the immune system of the host. Examples of such foreign, non-duck haptens include but are not limited to haptens associated with double-stranded DNA or RNA viruses, single-stranded DNA or RNA viruses, intracellular parasites, fungi, bacteria and cancer. Exemplary immunogens of particular importance are derived from bacteria such as *A. pertussis, S. parathyphoid* A and B, *C. diphtheriae, C. tetanus, C. botulinum, C. perifringens, A. anthracis, A. pestis, V. cholera, N. gonorrhea, H. inflienzae, T. palladium* and the like; and immunogens derived from viruses such as polio virus, adenovirus, parainfluenza virus, measles, mumps, respiratory syncytial virus, influenza virus, equine encephaloemeilitis, hog cholera virus, Newcastle virus, fowl pox virus, rabies virus, feline and canine distemper virus, foot and mouth disease virus, human and simian immunodeficiency viruses, and the like; rickettsiae immunogen such as epidemic and endemic typhus, and the spotted fever groups, and the like. Any hapten that can be inserted into the monomeric subunits of the particles of the present invention and to which it is desirable to elicit an immune response, may be utilized in the practice of the present invention. The sequence of duck HBcAg is known and the sequences of many appropriate haptens are known by those of skill in the art, as are the recombinant DNA techniques which are necessary for hapten insertion.

Several methods to confirm that the expressed particles contain the desired hapten are well known to those of skill in the art. For example, the sequence of the monomer may be determined by any of several well-known methods of amino acid sequencing.

In preferred embodiments of the present invention, a single copy of one hapten, several copies of one hapten, or copies of several different haptens may be inserted into a single region or several regions of the recombinant duck HBcAg monomer. The particle of the present invention is thus a highly versatile vehicle for the presentation of haptens, providing extensive flexibility in the design of immunogenic particles.

In preferred embodiments of the present invention, the regions into which the haptens may be inserted are those which, upon particle assembly, will elicit an immune response to the hapten. In a preferred embodiment of the present invention, the amino acids comprising the haptens are inserted in a manner such that they replace an equal number of amino acids of the recombinant monomer. In other embodiments, fewer or more or no recombinant monomer amino acids may be replaced by the hapten. In general, haptens of about 10 to 30 amino acids in length may be efficaciously inserted into a recombinant monomer. However, haptens of greater or lesser length may also be inserted. An inserted hapten (or haptens if more than one copy is inserted) will ultimately be flanked by amino-terminal and carboxy-terminal flanking sequences which correspond in sequence to duck HBcAg protein, or sequences which have been derived from duck HBcAg protein. In addition more than one copy of a hapten may be inserted at a single site, or at different sites on the same monomer, or different haptens may be inserted in tandem at a single site, or different haptens may be inserted at different sites on the same monomer. Any length and combination of haptens may be inserted so long as the monomer that is produced is able to assemble into particles which elicit an immune response.

The selection of regions into which haptens may be inserted may be made by comparison to the known primary sequence and three-dimensional structure of related hepatitis core antigen molecules., e.g. human HBcAg. See, for example, Bringas (1997) and Wynne, et al. (1999) for detailed discussions of human hepatitis virus core protein structure. Those of skill in the art will recognize that several methods exist for the comparative alignment of functional domains of related proteins such as human HBcAg and duck HBcAg.

In another preferred embodiment of the present invention, the particles of the present invention are comprised of monomers without a non-duck hapten. These particles may or may not contain nucleic acids. For example, a truncated form of duck HBcAg (t-duck HBcAg) from which the nucleic acid binding domain has been deleted, may be used as a general immune stimulatory agent (e.g. as an adjuvant) in and of itself. Further, particles comprised of monomers without a non-duck hapten may contain nucleic acids (either random nucleic acids from the recombinant host, or defined nucleic acids which are added during reassembly of the particles) and serve as a delivery mechanism for those nucleic acids. Defined nucleic acids may be delivered by the particle for the purposes of gene therapy or gene medicine, such as the delivery of anti-sense RNA, DNA sequences which encode a therapeutic agent, and the like.

In order to determine whether a particle is stimulating an immune response, a “stimulation index” may be measured. The stimulation index is a measure of the ability of a particle to effect an immune response and can be tested in various immune cell assays by measuring immune parameters, e.g. antibody forming capacity, number of lymphocyte subpopulations, mixed leukocyte response, lymphocyte proliferation, and the like. The stimulation of the immune response can also be measured in an assay to determine resistance to infection or tumor growth. Methods of measuring a stimulation index are well known to those of skill in the art. For example, one assay is the incorporation of $^3$H uridine in a murine B cell culture. The culture is contacted with 10 μg of particle for 20 hours at 37° C. and then pulsed with $^3$H uridine, 4 hours later cells are harvested and $^3$H uridine incorporated into RNA is measured. The induction of secretion of a particular cytokine can also be used to assess the stimulation index. Without meaning to be bound by theory, for use in vivo (e.g. to treat a subject at risk of exposure to a pathogenic agent) it is important that the particle be capable of effectively inducing cytokine secretion by monocytic cells and/or natural killer (NK) cell lytic activity. In one method, the stimulation index of the particle with regard to B-cell proliferation is at least about 5, preferably at least about 10, more preferably about 15, and most preferable at least about 20, while recognizing that there are differences in the stimulation index among individuals.

Due to their high level of versatility, the particles of the present invention may be of several types. Firstly, they may be either “non-mosaic” or “mosaic” in nature. By “non-mosaic” we mean a particle containing a single type of hapten. The monomers which make up non-mosaic particles may carry a single copy of a hapten or two or more copies of the same hapten. The hapten(s) may be inserted in a single region or in more than one region of the monomer.

Mosaic particles are particles which contain two or more different haptens. Mosaic particles may be either “intrinsic” or “extrinsic”. Intrinsic mosaic particles are those composed of monomers in which two or more different haptens are present on the same monomer. Intrinsic mosaic particles may be generated by genetically engineering two or more different haptens into a region or regions of a single monomer subunit.

Extrinsic mosaic particles are those containing two or more different haptens in which the different haptens are present on different monomers, and the particle is formed from a mixture of such monomers. One means of generating such extrinsic mosaic particles is to produce two or more different non-mosaic particles (or two or more different mosaic and non-mosaic particles), disassemble them into monomers, mix the monomers and allow them to reassemble into particles. Each reassembled particle will be comprised of a mixture of monomers of each type and will thus display a mixture of haptens.

The development of the extrinsic mosaic particles of the present invention was made possible by the discovery by Applicants that recombinant duck HBcAg particles can be reversibly disassembled under mild, non-denaturing conditions. This discovery allows the relatively facile production of a wide variety of extrinsic mosaic particles containing from one to several hundred different haptens per particle for presentation to the immune system. In this way, the particles of the present invention may be used to immunize against a plethora of quasispecies in a single immunization. This is a significant improvement over previous hapten carriers.

The reason that recombinant duck HBcAg particles can be disassembled under mild conditions is that the monomers have only a single cysteine residue and it is present in the free, sulfhydryl form. In contrast, human HBcAg monomers are connected to one another in the particle by numerous disulfide bonds, requiring harsh conditions to disassemble the particle.

The ability to disassemble and reassemble the particles of the instant invention provides a way of carrying out another facet of the present invention. Recombinant duck HBcAg monomers have an intrinsic ability to bind nucleic acid molecules as a result of possessing a nucleic acid binding domain (arginine rich amino acid residues 201-262). The natural function of the nucleic acid binding domain is to allow Hepatitis B viral particles to bind and "package" their own genetic material and thus transport it from cell to cell and from host to host during an infection. The particles of the present invention, when isolated from, for example, an E. coli recombinant expression system, carry within themselves a short, heterogeneous population of random nucleic acids from the bacterial host. The particles of the present invention may be disassembled, the monomers may be separated from the host nucleic acid, and the monomers may then be reassembled in the presence of a different nucleic acid of choice. The nucleic acid of choice will be bound by the monomers and "packaged" into the reassembled particle.

The particles of the present invention may be reassembled to contain any nucleic acid of choice. Examples of such nucleic acids include but are not limited to single- and/or double-stranded DNA and/or RNA, (or DNA/RNA hybrids). The nucleic acids may be delivered for any therapeutic purpose, for example, in order to be transcribed or translated into a therapeutic entity or to bind to other nucleic acids already present in the body in order to enhance or prevent the transcription or translation of those nucleic acids. For use in the instant invention, the nucleic acids can be synthesized de novo using any of a number of procedures well known in the art. For example, the β-cyanoethyl phosphoramidite method (Beuacage and Caruthers, 1981); nucleoside H-phosphonate method (Garegg et al, 1986; Froelder et al., 1986; Garegg er al, 1986; and Gaffney et al., 1988). These chemistries can be performed by a variety of automated oligonucletide synthesizers available in the market. Alternatively, oligonucleotides can be prepared from existing nucleic acid sequences (e.g. genomic or cDNA) using known techniques such as those employing restriction enzymes, exonucleases, or endonucleases.

For use in vivo, nucleic acids are preferably resistant to degradation (e.g. via endo- and exo-nucleases). Secondary structures, such as stem loops, can stabilize nucleic acids against degradation. Alternatively, nucleic acid stabilization can be accomplished via phosphate backbone modifications. A preferred stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made, e.g. as described in U.S. Pat. No. 4,469,863; and alkylphosphotriesters (in which the charged oxygen moiety is alkylated as described in U.S. Pat. No. 5,023,243 and European Patent No. 092, 574) can be prepared by automated solid phase synthesis using commercially available reagents. Methods for making other DNA backbone modifications and substitutions have been described (Uhlmann and Peyman, 1990; Goodchild, 1990).

The nucleic acids can include the use of phosphothioate or phosphodithioate rather than phosphodiesterase linkages within the backbone of the molecule, or methylphosphorothiate terminal linkages (Kreig et al., 1996; Bogg, et al., 1997). The phosphate backbone modification can occur at the 5' end of the nucleic acid, for example at the first two nucleotides of the 5' end of the nucleic acid. The phosphate backbone modification can occur at the 3' end of the nucleic acid, for example at the first two nucleotides of the 3' end of the nucleic acid. Nontraditional bases such as inosine and queosine, as well as acetyl-, thio- and similarly modified forms of adenine, cytidine, guanine, thymine and uridine can also be included, which are not as easily recognized by endogenous endonucleases. Other stabilized nucleic acid molecules include: nonionic DNA analogs, such as alkyl- and aryl phosphonates (in which the charged oxygen moiety is alkylated). Nucleic acid molecules which contain a diol, such as tetrahyleneglycol or hexaethyleneglycol, at either or both termini, are also included. The term "oligonucleotide" includes both single and double stranded forms of DNA.

In a preferred embodiment of the present invention, the particles of the present invention will be reassembled to contain immune stimulating nucleic acids. Such immune stimulating nucleic acids have been recently described (Carson and Raz, 1997; Davis et al., 1998; Kreig et al., 1995; Lipford et al, 1997a; Lipford et al, 1997b; Pisetsky, 1996; Sparwasser et al., 1997; Sparwasser et al., 1998; Stacey et al., 1996; Sun et al., 1998; and Zimmerman et al, 1998). DNA was first described as an immune stimulator when it was observed that bacterial DNA caused regression of transplantable tumors in vivo without direct tumor cytotoxicity. This tumor resistance induced by DNA resulted from increased natural killer (NK) cell activity. NK activity could be stimulated by DNA from a variety of bacterial sources but not by mammalian DNA, indicating that base modifications and/or nucleotide sequence, rather than the DNA backbone, is the critical mediator of NK stimulation. Studies assessing the immune stimulatory activity of randomly chosen oligonucleotides indicated that a defined motif (RACGTY, where R=A or G and Y=C or T) caused a potent induction of NK cells. With respect to mammalian DNA, this sequence is under-represented and when this sequence is found in mammalian DNA, it is masked by modification. Experiments have determined that oligonucleotides with these modified sequences have no NK or other immune stimulatory activity. The mechanism of immune stimulation by these nucleic acids is as yet unknown. It is known that the production of cytokines IL-12, TNF-α, IL-6, and IL-1 in antigen presenting cells (APC) is stimulated. Initial studies indicate that the individual levels of these cytokines can be modulated by changing the sequence surrounding the defined immune stimulating motif.

The use of immune stimulating nucleic acids in vaccines has been previously described. For example, U.S. Pat. No. 5,723,335 to Hutcherson et al. and PCT International Application Publication Number WO 98/40100, both of which are incorporated herein by reference, describe the use of immunopotentiating nucleic acids to enhance immune responses to vaccines. However, the delivery mechanism is simply to inject the nucleic acids along with other vaccine components, a method which may not deliver sufficient quantities of nucleic acids in an efficacious manner.

Bacterial DNA appears to enter immune cells by bulk phase endocytosis or protocytosis where it is then processed by antigen presenting cells. Antigen presenting cells appear to process the particles of the present invention either by bulk phase endocytosis or receptor mediated endocytosis. By including the immune stimulating nucleic acids as an intrinsic part of the particle, they will be carried into the host in concentrated form and processed directly by antigen presenting cells, maximizing their effect as adjuvants.

In a preferred embodiment of the present invention, the immune stimulating nucleic acids will be characterized by oligonucleotides with the base sequence 5'-RACGTY-3' (SEQ ID #20) surrounded by up to 20 nucleotides on either side. Preferably the immune stimulatory oligonucleotide is in the range of about 8 to 30 bases in size. For use in the instant invention, the nucleic acids can be comprised of various modified bases as listed above, and synthesized de novo using any of a number of procedures well known in the art as listed above. For example, International Patent Application WO 95/26204, entitled "Immune stimulation by phosphorothioate oligonucleotide analogs" reports the non-sequence-specific immunostimulatory effect of phosphorothioate modified oligonucleotides. Alternatively, CpG dinucleotides can be produced on a large scale in plasmids (Sambrook et al., 1989) which after being administered to a subject are degraded into oligonucleotides. Oligonucleotides can be prepared from existing nucleic acid sequences (e.g. genomic or cDNA) using known techniques, such as those employing restriction enzymes, exonucleases, or endonucleases.

The immune stimulatory nucleic acids may stimulate cytokine production (e.g. IL-6, IL-12, IFN-γ, TNF-α and GM-CSF). Exemplary sequences include but are not limited to:

```
TCCATGTCGCTCCTGATGCT       (SEQ ID #3)
TCCATGTCGTTCCTGATGCT       (SEQ ID #4)
TCGTCGTTTTGTCGTTTTGTCGTT   (SEQ ID #5)
```

The immune stimulatory nucleic acids may stimulate natural killer cell (NK) lytic activity in a subject. Specific but nonlimiting examples of such sequences include:

```
TCGTCGTTGTCGTTGTCGTT       (SEQ ID #6)
TCGTCGTTTTGTCGTTTTGTCGTT   (SEQ ID #7)
TCGTCGTTGTCGTTTTGTCGTT     (SEQ ID #8)
GCGTGCGTTGTCGTTGTCGTT      (SEQ ID #9)
TGTCGTTTGTCGTTTGTCGTT      (SEQ ID #10)
TGTCGTTGTCGTTGTCGTT        (SEQ ID #11)
TCGTCGTCGTCGTT.            (SEQ ID #12)
```

The immune stimulatory nucleic acids may stimulate B cell proliferation. Specific, but nonlimiting examples of such sequences include:

```
TCCTGTCGTTCCTTGTCGTT       (SEQ ID #13)
TCCTGTCGTTTTTTGTCGTT       (SEQ ID #14)
TCGTCGCTGTCTGCCCTTCTT      (SEQ ID #15)
```

-continued

```
TCGTCGCTGTTGTCGTTTCTT      (SEQ ID #16)
TCGTCGTTTTGTCGTTTTGTCGTT   (SEQ ID #17)
TCGTCGTTGTCGTTTTGTCGTT     (SEQ ID #18)
TGTCGTTGTCGTTGTCGTT.       (SEQ ID #19)
```

Any appropriate immune stimulating nucleic acid may be utilized in the practice of the present invention.

The present invention provides a method for the disassembly and reassembly of the particles of the present invention under relatively mild, physiological conditions. In general, the method entails 1) providing particles comprised of a plurality of nucleocapsid protein monomers, the primary amino acid sequences of which are derived from duck hepatitis B virus, wherein said plurality of monomers are assembled to form a particle; 2) exposing the particles to a charged agent; and 3) removing the charged agent. Upon removal of the charged agent, the monomers spontaneously reassemble into particles. A preferred embodiment of the method is as follows: Particles may be isolated from a recombinant expression system by a simple four-step method. For example, cells are pelleted by centrifugation and lysed by a French press. Ammonium sulfate is added to 277 g/L. Precipitated material is collected by centrifugation and resuspended in phosphate buffer and dialyzed against phosphate buffer overnight. The resulting dialysate is applied to a hydroxyapatite column and washed with phosphate buffer until the optical density at 280 nm is below 0.1.277 g/L of ammonium sulfate is added to the pooled fractions and the precipitate collected by centrifugation. The resulting pellet is resuspended in minimal buffer and applied to a Sepharose-CL4B size exclusion chromatography column. Peak fractions representing the particles are determined by SDS-PAGE and pooled. The particles are resuspended in neutral buffer (e.g. 20 mM Tris HCl, pH 7.0) and high (0.1 to 1 M) divalent cation concentrations, such as $Mg^{+2}$, $Zn^{+2}$, $Ba^{+2}$, $Ca^{+2}$, $Pb^{+2}$ and $Sr^{+2}$. The particles are allowed to dissociate into monomers (with gentle mixing) for approximately 1 hour and the progress of dissociation may be monitored by Fast Protein Liquid Chromatography (FPLC) Sepharose-CL4B size-exclusion column chromatography, or native agarose gel electrophoresis. Ribonuclease A may be added to remove nucleic acids (e.g. recombinant host nucleic acids) which were contained within the particles as originally isolated. Reassembly is effected in the following manner: For the truncated form of duck HBcAg (t-duck HBcAg), from which the nucleic acid binding domain has been deleted, reassembly and particle formation occurs upon simple dialysis against an appropriate buffer plus 100-200 mM NaCl. The non-truncated form of duck HBcAg reassembles only in the presence of nucleic acids. Thus, the monomers may be mixed with the nucleic acid of choice, dialyzed against an appropriate buffer, upon which dialysis reassembled particles containing the nucleic acid are formed. In a preferred embodiment of the present invention the molar ratio of nucleic acid to monomer is about 1:1. Exogenous DNA which was not incorporated into the reassembled particles may be removed by size-exclusion column chromatography. Those of skill in the art will recognize that many minor variations in the practice of the method of the present invention may be undertaken without significantly altering the outcome of the method. For example, the procedure may be "scaled up" or "scaled down" for production purposes. In addition, some variations may be beneficial for optimizing the procedure for a particular monomer type, e.g. variations in ionic strength, pH, exact ratio of nucleic acid to monomer, and the like. All such variations and optimizations are included in the scope of the method of the present invention.

The disassembly/reassembly process is illustrated in FIG. 3. In this figure, a particle 10 is comprised of duck HBcAg monomers 11 containing a hapten specific for, for example, pertussis, and a particle 20, is comprised of duck HBcAg monomers 21 containing a hapten specific for, for example, polio.

Particles 10 and 20 are exposed to a charged agent (e.g. a divalent cation) upon which exposure particles 10 and 20 disassemble into monomers 11 and 21. Unwanted nucleic acids which were contained within the particles may be removed, for example, by the addition of a nuclease. After removal of the nuclease, specific nucleic acids 30 may be added to the mixture of monomers 11 and 21. Upon removal of the charged agent, the monomers 11 and 21 reassemble to form an extrinsic mosaic particle 40, which contains nucleic acids 30.

In another aspect of the present invention, the foreign, non-duck hapten(s) may be attached to the particle rather than genetically engineered into the monomer sequence. The individual polypeptide haptens (for example a polypeptide, carbohydrate, and the like) can be operatively linked to the particle through an amino acid residue side chain to form an immunogenic conjugate, i.e. a branched-chain polypeptide and/or polypeptide/carbohydrate polymer. Such particles are to be considered "derived from" duck HBcAg as described above and are contemplated for use within the practice of this invention.

The present invention provides particles for use in eliciting an immune response in a host. In a preferred embodiment of the present invention, the particles may be used as a vaccine in the classical sense, i.e. prophylactically in order to prime the host immune system prior to exposure to a disease causing entity. In yet another preferred embodiment of the present invention, the particles of the present invention may be used therapeutically, i.e. to boost the immune response of a subject against a pathogen which has already infected the subject, for example in the case of HIV infection.

The present invention also provides a composition for use in eliciting an immune response comprising the particles of the present invention. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain other adjuvants. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of active ingredient in the formulations may vary. However in general, the amount of active ingredient (particles) in the formulations will be from 1-99%.

The present invention also provides a method for eliciting an immune response in a subject, comprising administering to said subject an effective amount of a composition comprising the particles of the present invention. By effective amount we mean an amount of the composition of the present invention necessary to prevent, cure or at least partially arrest the symptoms of the subject. The subject may be any vertebrate, for example, any mammalian (e.g. human) or avian species. The exact amount of the compound to be administered will vary from subject to subject and may depend on, for example, weight, gender, age, overall physical condition and the like. Such variables well understood by those of skill in the art and are best assessed by skilled practitioners in the art.

The compositions of the present invention may be administered in any of a variety of ways which are well known to those of skill in the art and include but are not limited to: parenterally (e.g. subcutaneously or by intradermal or intramuscular injection), orally, opthalmically, vaginally, rectally, intranasally, transdermally, and the like. Any appropriate method of administration may be utilized in the practice of the present invention so long as the compositions are delivered in an effective manner.

The following examples illustrate are given in order to illustrate several aspects of the invention, and should not be interpreted in any way to restrict the applications of the invention.

EXAMPLES

Materials

Duck HBcAg particles: Duck HBcAg particles were obtained from an *E. coli* recombinant expression system. The duck HBcAg particles have the amino acid sequence depicted in FIG. 1 (SEQ ID #1) and may contain a heterogeneous population of host-derived nucleic acids. The duck HBcAg (1-239) particles have the amino acid sequence depicted in FIG. 17 (SEQ ID #21) and the nucleic acid sequence depicted in FIG. 18 (SEQ ID #22). The t-duck HBcAg particles have the amino acid sequence depicted in FIG. 19 (SEQ ID #23) and the nucleic acid sequence depicted in FIG. 20 (SEQ ID #24) t-duck HBcAg ("truncated" duck HBcAg) particles are composed of monomeric subunits in which the nucleic acid binding domain has been deleted by genetic engineering.

Methods

Quantization of specific RNAs. Specific RNAs produced by J774A.1 macrophage cells were quantified after exposure to different types of stimuli: 1) duck HBcAg particles which contained nucleic acids or 2) t-duck HBcAg particles which do not contain nucleic acids. Cells were treated with 10 μg of either duck HBcAg or t-duck HBcAg and total RNA was isolated from duplicate samples at various time points. Total RNA was reverse transcribed using random hexamers, and PCR was then performed in the linear range using gene specific primers. PCR products were analyzed by gel electrophoresis and quantified by densitometry. Prior to use, recombinant proteins were treated with Triton X-114 three times to remove lipopolysaccharide contaminants.

Quantization of IL-12: Capture ELISA was used to determine IL-12 p70 protein in cell culture media and cell extracts with R&D ELISA kit. IL-12's biologically active form is a heterodimeric disulfide linked glycoprotein consisting of p35 and p40 subunits. IL-12 is produced by activated antigen presenting cells including macrophages, dendritic cells, and B cells. Following activation p40 expression is induced and translated. The resulting p40 protein binds to the constitutively expressed p30 subunit and is secreted to perform various biological functions. A capture ELISA was used to determine the concentration of IL-12 secreted by dendritic cells and secreted and located intracellularly in J774A.1 macrophages following treatment with increasing amounts of duck HBcAg. Microplates (12 strips of 8 wells/plate) coated with an antibody to capture IL-12 p70 were incubated with cleared cell culture media or cell extracts following an 18 hour exposure to duck HBcAg. This mixture was allowed to incubate for 2 hours. Following incubation wells were washed 5 times with wash buffer. Following washing, buffer containing an anti-p70 antibody conjugated to horse radish peroxidase which binds to a separate binding motif than the capture antibody, is added and incubated for 2 hours at room temp. After incubation the wells are washed once again 5 times. A colorimetric substrate that reacts with the horse radish peroxidase is added for 30 minutes at room temperature, in the dark. After 30 minutes an acidic solution is added to terminate the reaction. The absorbance of each sample is then measured at 450 nm and corrected at 540 nm. Results are compared to standard reactions performed at the same time under the same conditions and are given in the units pg/ml.

Flow cytometry: Cell markers CD4+, CD8+, Ly-6A/E and B7-2 were monitored by flow cytometry in the following manner:

Cell Culture: J774A.1 cells were split to 500,000 cells per well one day prior to the experiment. On the day of the experiment LPS-free duck HBcAg was added directly to the cell culture media to the appropriate concentration and allowed to incubate with the cells for 18 hours. At 18 hours cells were dislodged by pipetting, centrifuged at 500×g for 10 minutes and then washed 3 times in phosphate buffered saline. Cells are then incubated with 10 μg/ml Mouse IgG in phosphate buffered saline (PBS) with 1% bovine serum albumin (BSA) to block Fc receptors. Fluorocein isothiocyanate (FITC) conjugated primary antibodies against mouse B7.2 (CD86), H-2k$^b$ (MHC-I), I-A$^b$ (MHC-II); Ly6A/E and Ly6/C were added respectively and incubated 30 minutes at 4° C. Fluoroscein isotype matched non-specific antibodies were used as the negative control. At least 10$^5$ cells were collected for data analysis. Cells were pelleted by centrifugation and non-bound antibody was washed away with three washes with PBS with 1% BSA. Cells were then resuspended in FACS buffer and cell surface markers quantified by Beck-Dickson FACscanner. Similar methods were used for spleenocytes except the antibodies against mouse CD8RPE and CD4-RPE (R-phycoerythrin) were also included.

Quantization of IgG titer, both total and isotypic: Mice were immunized with lipopolysaccharide free duck HBcAg (0, 1 or 10 μg) without adjuvant. At 10 days, 24 days, and then 14 days following secondary immunization, blood was drawn and tested for duck HBcAg antibodies. Approximately 100 ul of blood was drawn by retro-orbital puncture. Following the bleed samples were allowed to clot. Clots were removed by centrifugation and the resulting serum contained the IgG fraction. Serum samples were serial diluted from 10(1) to 10(6).

ELISA plates coated with duck HBcAg protein (in the particulate form) were prepared by incubating commercially available ELISA plates with duck HBcAg protein in bicarbonate buffer overnight at room temperature. Plates were washed 5 times with washing buffer then blocked for non-specific binding with bovine serum albumin (BSA) for two hours at room temperature. Plates were washed 5 times with washing buffer and stored at 4° C. prior to use.

100 ul of diluted serum samples were incubated with pre-coated plates for 2 hours at room temperature. Following incubation, wells were washed 5 times with wash buffer. Following washing, buffer containing a rat anti-mouse IgG antibody conjugated with horse radish peroxidase is added and incubated for 2 hours at room temp. After incubation the wells are washed once again 5 times. A colorimetric substrate that reacts with the horse radish peroxidase is added for 30 minutes at room temperature, in the dark. After 30 minutes an acid stop solution is added and the reaction is terminated. The absorbance at 450 nm of each sample is then measure at 450 nm and corrected at 540 nm. Results are compared to standard reaction performed at the same time under the same conditions and are given in the units of relative titers.

For isotype specific assay, rat anti-mouse antibody specific for the antibody isotype was used instead of the general rat anti-mouse antibody. All other conditions remained the same.

Method for Disassembling and Reassembling Duck HBcAg, Duck HBcAg(1-239) and t-duck HBcAg It has been discovered that duck HBcAg, duck HBcAg (1-239) and t-duck HBcAg particles can be reversibly assembled between the monomeric and particulate forms. This process may be carried out under non-denaturing conditions in neutral buffer (e.g. Tris HCl pH 7.0) and high concentrations (e.g. 0.1-1 M) of divalent cations such as Mg$^{+2}$, Zn$^{+2}$, Ba$^{+2}$, Ca$^{+2}$, Pb$^{+2}$ and Sr$^{+2}$. The particles as isolated from the recombinant expression system are allowed to dissociate into monomers (with gentle mixing) for approximately 1 hour and the progress of dissociation is monitored by FPLC (Pharmaica) Sepharose-CL4B size-exclusion column chromatography, or by native agarose gel electrophoresis. Ribonuclease A (e.g. 7.5 μg/mL) is added to remove recombinant host nucleic acids which were contained in the particles as isolated Reassembly is effected in the following manner: The non-nucleic acid binding t-duck HBcAg monomers can reassemble by simple dialysis in neutral buffer containing 100-200 mM NaCl. The duck HBcAg and duck HBcAg(1-239) monomers are dependent upon the presence of nucleic acids for appropriate reassembly. The monomers are mixed with the nucleic acid of choice and dialyzed against neutral buffer, upon which dialysis reassembled particles containing the nucleic acid are formed. The preferred molar ratio of monomer to oligonucleotide is 1:1. Exogenous DNA which is not incorporated into the reassembled particles may be removed by size-exclusion column chromatography.

Example 1

Induction of Cytokines in vitro

Figure 4A:
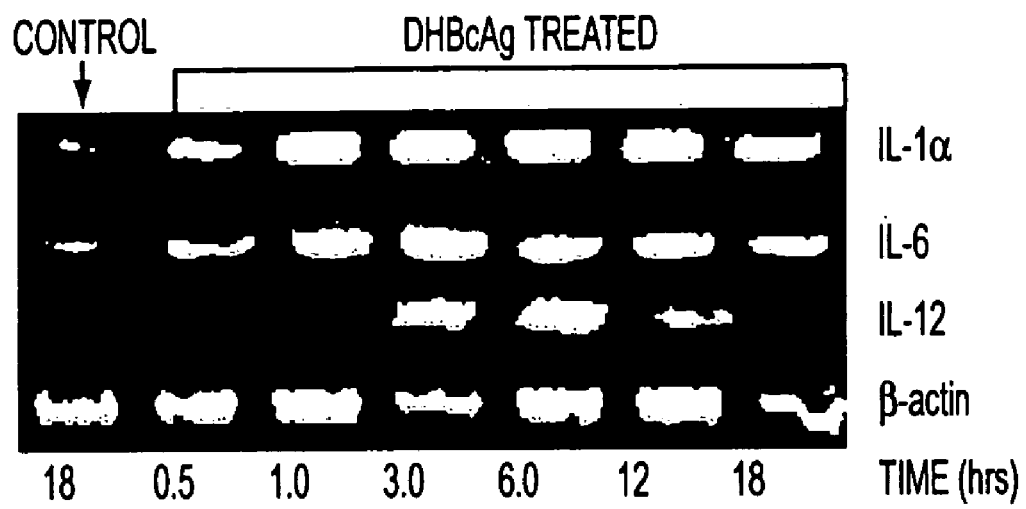
FIGS. 4A and 4B. Analysis of specific RNAs in J774A.1 macrophage cells after exposure to recombinant duck HBcAg particles (4A) or recombinant t-duck HBcAg particles (4B). RNA was detected by reverse transcriptase polymerase chain reaction (RT-PCR) and visualized by agarose gel electrophoresis.
Figure 4B:
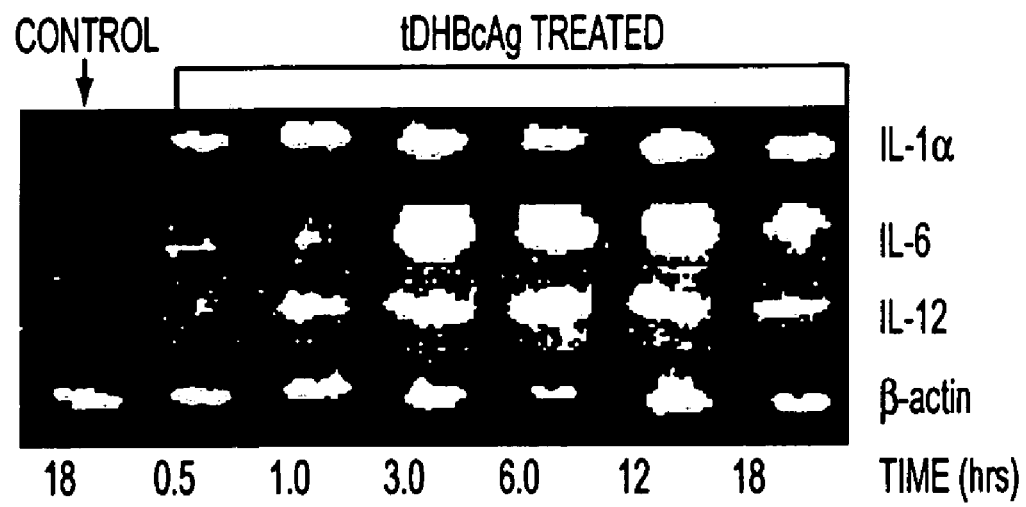

Experiments were conducted as described in Methods in order to determine which, if any, cytokines were induced by the exposure of J774A.1 macrophage cells to recombinant duck HBcAg and t-duck HBcAg. The results are given in FIG. 4. As can be seen, increased transcription of the TH 1-type cytokines IL-1α, IL-6 and IL-12 was induced by both duck HBcAg and t-duck HBcAg, indicating that the core protein is responsible for the induction of a TH1 cytokine profile.

Example 2

Induction of IL-12 p70 Protein Production

Figure 5A:
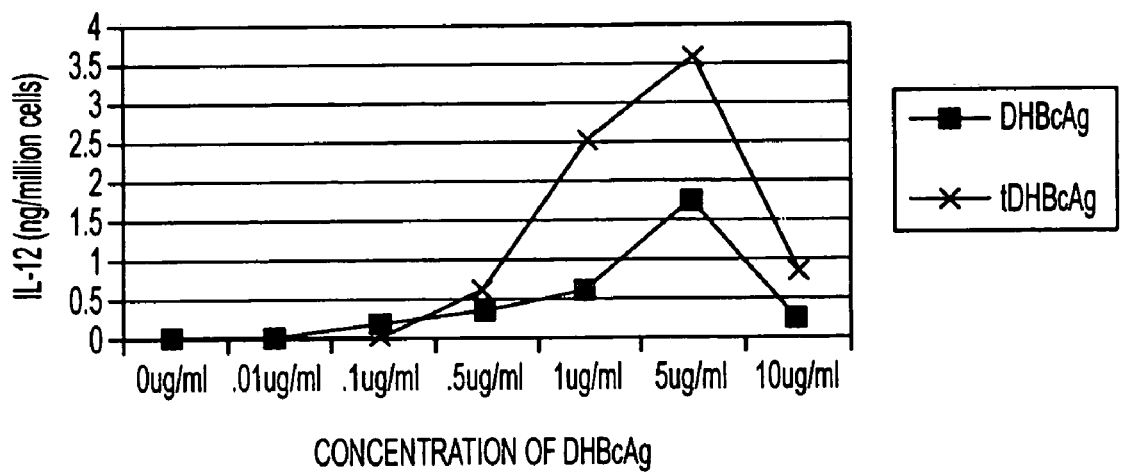
FIGS. 5A and 5B. Concentration of IL-12 in the culture medium (5A) or the cell extract (5B) of J774A.1 macrophage cells following treatment with recombinant duck HBcAg particles or recombinant t-duck HBcAg particles for 72 hours.
Figure 5B:
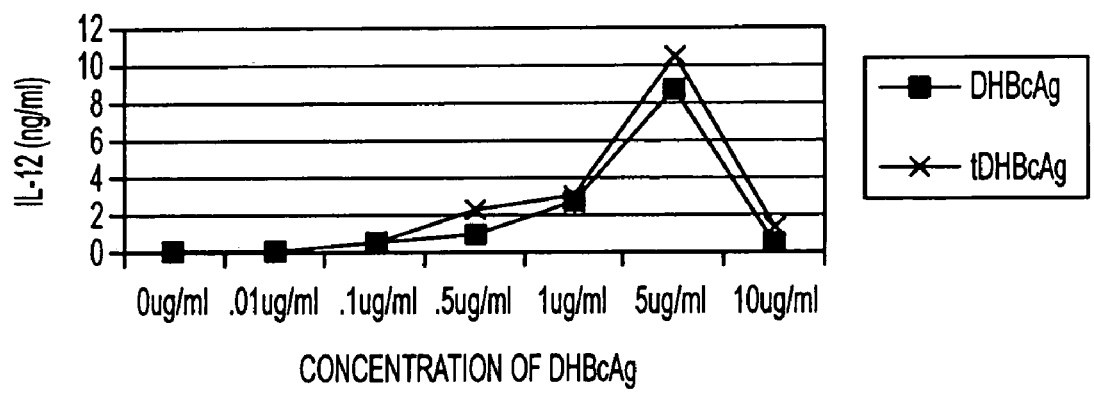
Figure 6:
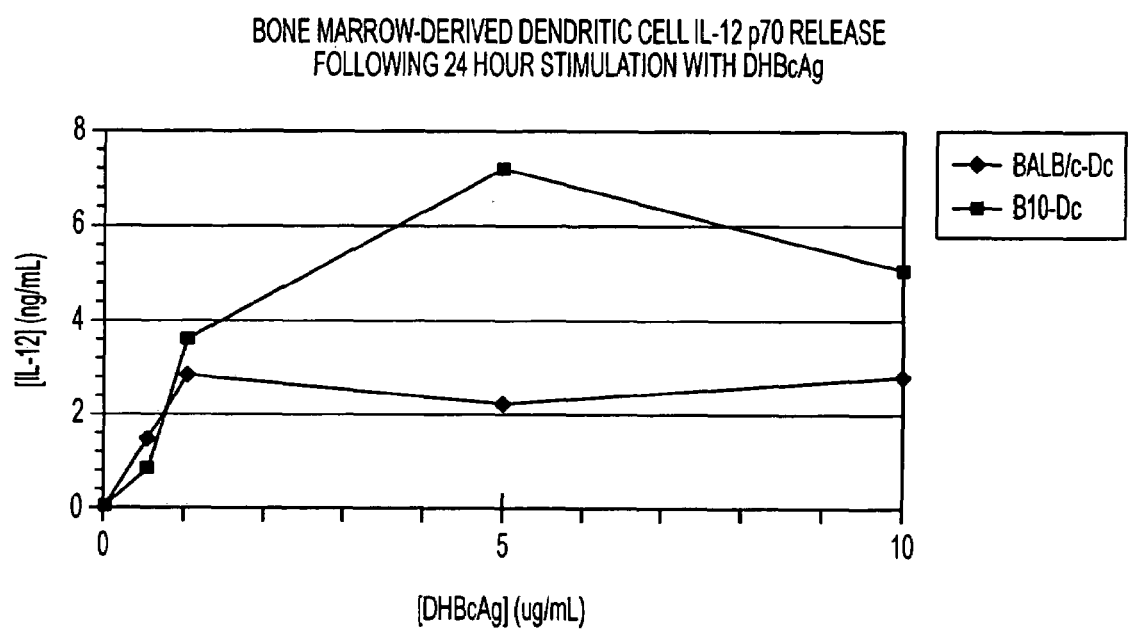
FIG. 6. Concentration of IL-12 in the culture medium of bone marrow-derived dendritic cells from BALB/C and B10 mice following treatment with recombinant duck HBcAg particles for 24 hours.

Experiments were conducted in vitro to determine whether the addition of duck HBcAg and t-duck HBcAg to J774A.1 macrophage cells and the addition of duck HBcAg to mouse bone marrow-generated dendritic cells induced production of IL-12 p70 protein. Analysis of the quantity of IL-12 p70 in the cell culture media and cell extracts was carried out as described in Methods and the results are given in FIGS. 5A, 5B and 6. As can be seen, exposure to duck HBcAg and t-duck HBcAg for 72 hours increased the concentration of IL-12 in the culture medium (FIG. 5A) and in the cells themselves (FIG. 5B) of J774A.1 macrophage cells. Exposure of mouse bone marrow-generated dendritic cells from both BALB/C and B10 mice to duck HBcAg for 24 hours resulted in an increase in IL-12 in the culture medium (FIG. 6). This response is consistent with the induction of a TH1-type immune response.

Example 3

Analysis of Cell Markers on J774A.1 Macrophage Cells

Experiments were conducted in vitro to determine whether the addition of duck HBcAg and t-duck HBcAg to J774A.1 macrophage cells could induce the presence of cell markers MHC-I, MHC-II, Ly-6A/E and B7-2. These cell surface markers are directly implicated in a TH1 type immune response. The presence of cell markers was determined by flow cytometry as described in Methods. The results are given in FIG. 6. As can be seen, the data showed that each type of cell surface antigen was upregulated after treatment with duck HBcAg for 18 hours, indicating that macrophages can be stimulated by duck HBcAg and t-duck HBcAg.

Example 4

Immunogenicity of Duck HBcAg

Figure 7A:
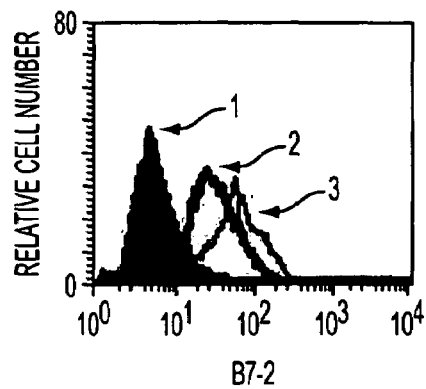
FIGS. 7A, 7B, 7C, 7D and 7E. Flow cytometry analysis of cell surface antigen expression in J774A.1 macrophage cells after treatment with recombinant duck HBcAg particles. 7A: CD86; 7B: MHC I; 7C: MHC II; 7D: Ly-6A/E; 7E: Ly-6C. Arrows: 1, shaded area: isotype control; 2, solid line: non-treated control; 3, dotted line: treated with 10 μg recombinant duck HBcAg particles.
Figure 7B:
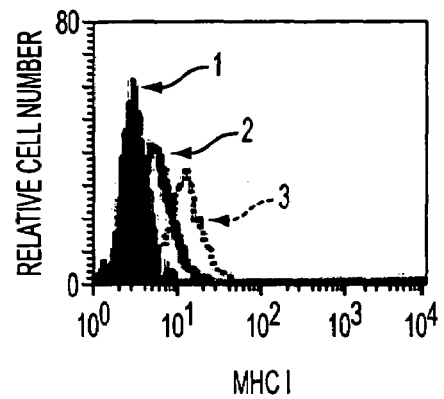
Figure 7C:
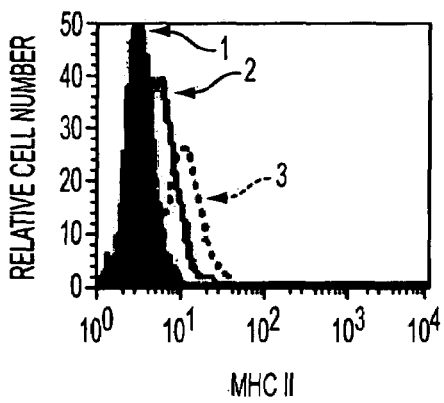
Figure 7D:
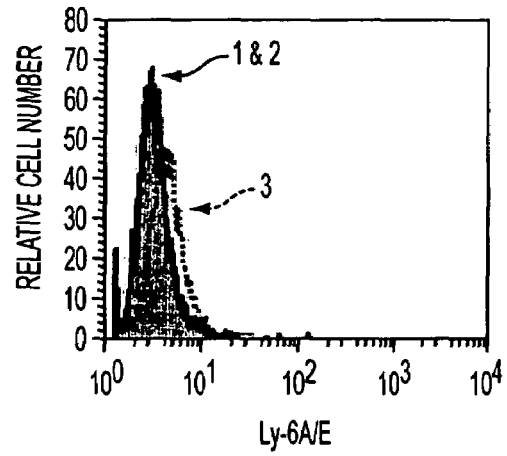
Figure 7E:
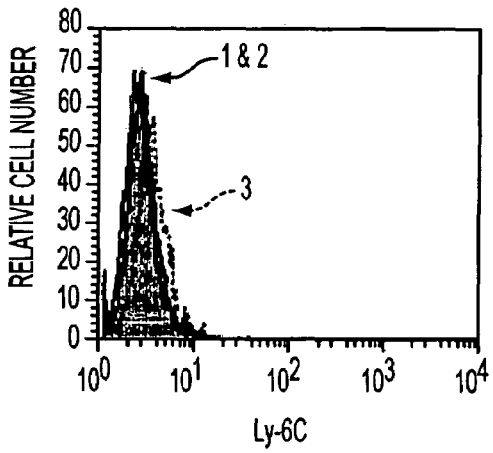
Figure 8A:
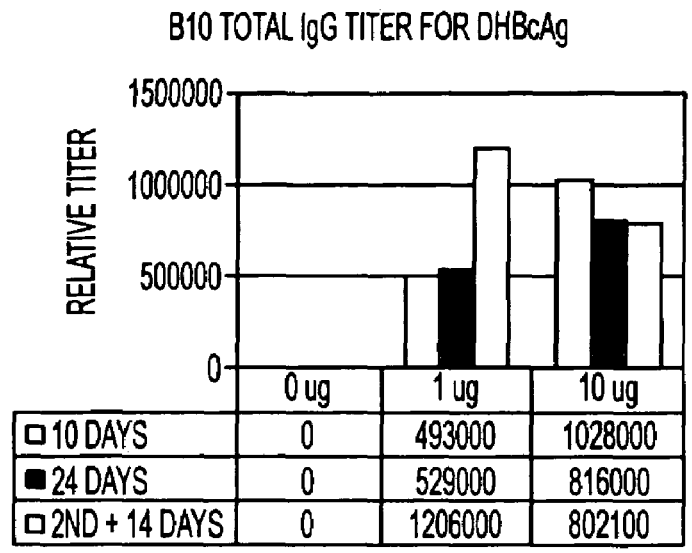
FIGS. 8A and 8B. Total IgG titer for duck HBcAg in vivo. 8A: B10 mice. 8B: BALB/C mice.
Figure 8B:
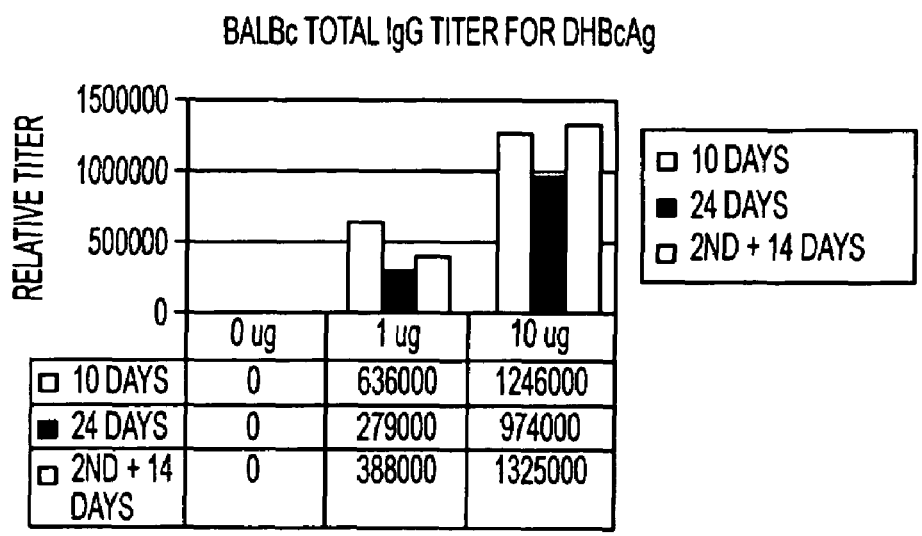

The immunogenicity of duck HBcAg was tested by determining the total IgG titer for duck HBcAg in the following manner: two strains of mice, B10 and BALB/C, were immunized as described in Methods. The results are given in FIG. 7. As can be seen, both B10 (FIG. 7A) and BALB/C (FIG. 7B) mice generated antibody titers greater than $10^5$, indicating that duck HBcAg is highly immunogenic. Further, the isotype of the IgG fraction, depicted in FIG. 8, shows a TH1 bias via the production of IgG2a, IgG2b and IgG3. Of particular importance is the fact that BALB/C mice showed a TH1 bias even though their genetic background is normally biased for a TH2 immune response.

Example 5

Analysis of Cell Markers on Spleenocytes

Figure 9:
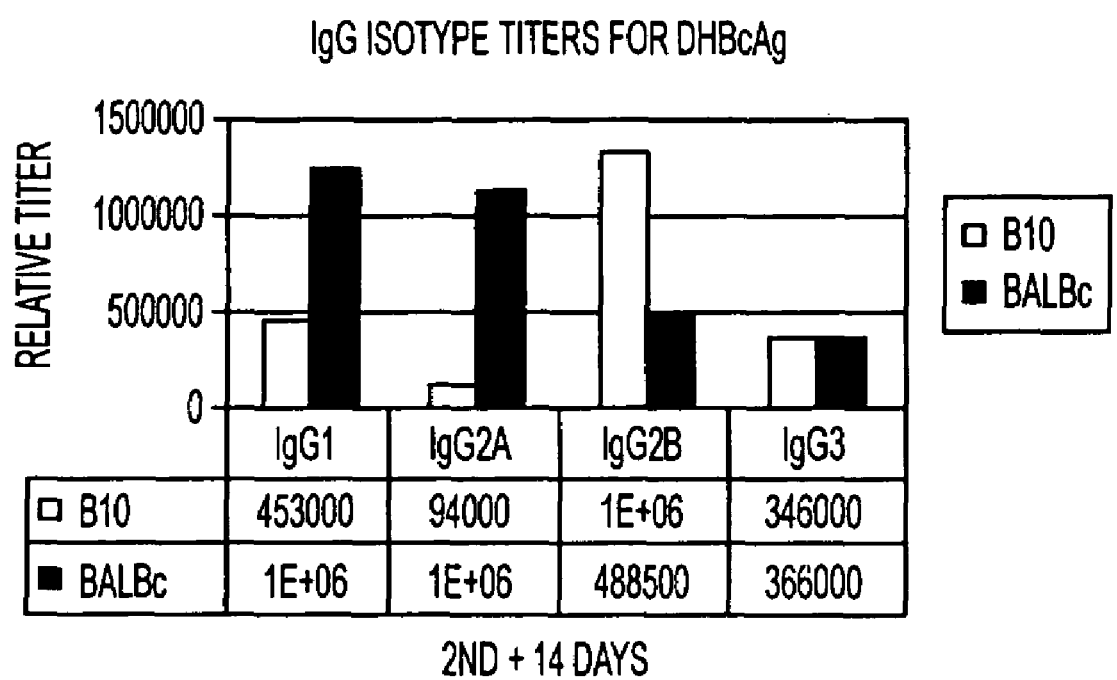
FIGS. 9. IgG isotype titers for duck HBcAg in B10 and BALB/C mice.
Figure 10A:
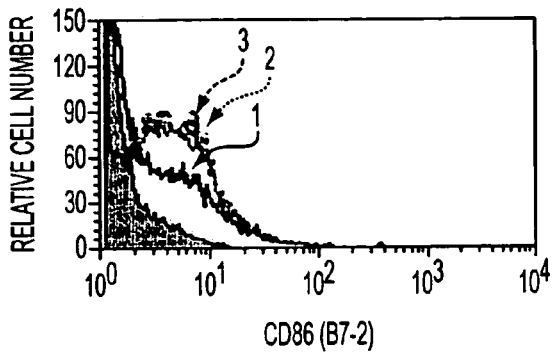
FIG. 10A, 10B, 10C and 10D. Flow cytometry analysis of cell surface antigen expression in spleenocytes following re-stimulation with 1 μg duck HBcAg in vitro for 24 hours. 10A: CD86; 10B: Ly-6C; 10C: CD4+; 10D: CD8+. Arrows: 1, immunized with 0 μg of duck HBcAg. 2, immunized with 1 μg of duck HBcAg. 3, immunized with 10 μg of duck HBcAg.
Figure 10B:
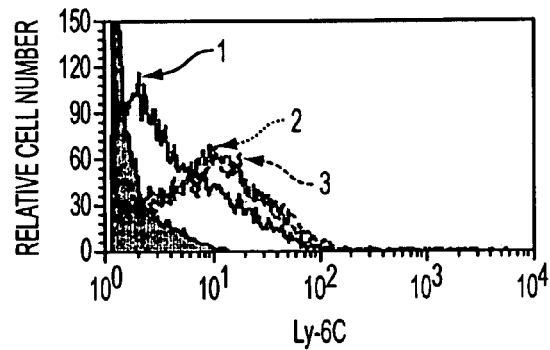
Figure 10C:
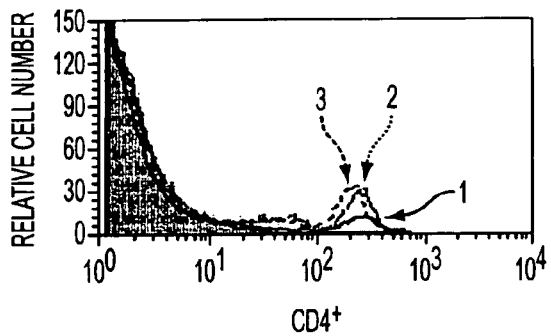
Figure 10D:
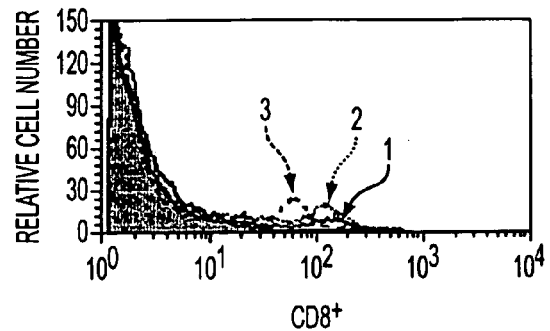

Following the terminal bleed, spleenocytes were obtained from the B10 mice and cultured with 1 μg of duck HBcAg for 24 hours. Flow cytometry (as described in Methods) was used to monitor cell markers CD4+, CD8+, Ly-6A/E and B7-2. The results are presented in FIG. 9. As can be seen, both the 1 μg and 10 μg immunized mice had substantial increases in the presence of these cell markers over control cells from non-immunized mice, indicating a strong T-cell response.

Example 6

Figure 11A:
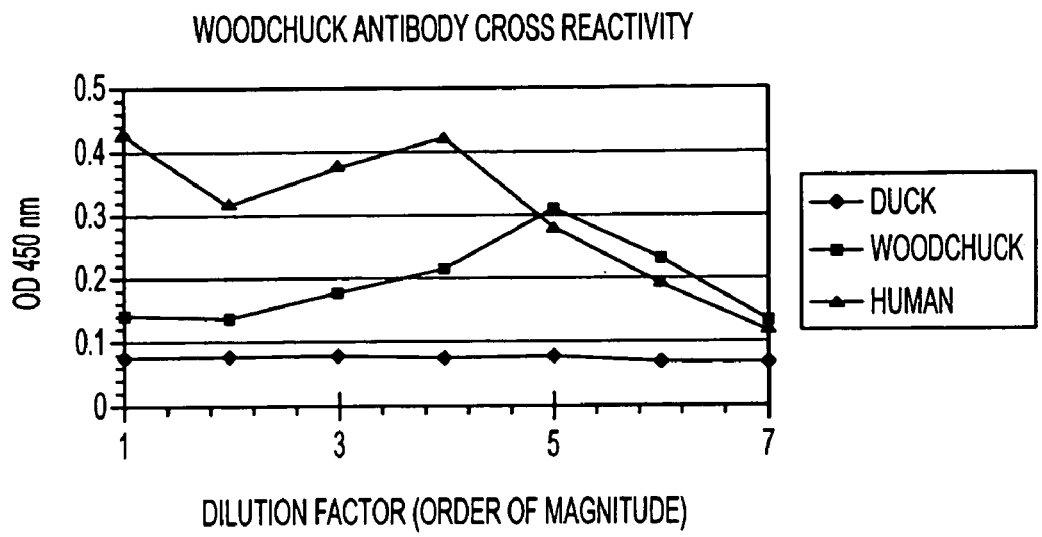
FIGS. 11A and 11B. Comparison of crossreactivity of woodchuck with duck and human antibodies (11A) and crossreactivity of human with duck and woodchuck antibodies (11B).
Figure 11B:
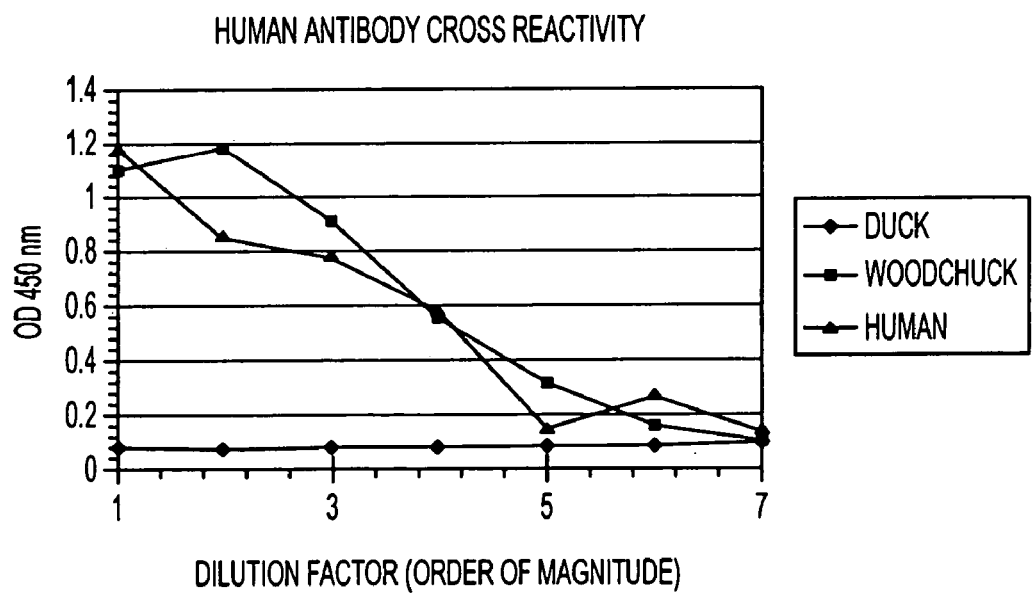

Demonstration of Lack of Crossreactivity of Duck HBcAg with Human and Woodchuck HBcAg Experiments were conducted as described in Methods in order to compare the crossreactivity of duck, woodchuck and human HBcAg. As can be seen in FIG. 11A, woodchuck antibody displays extensive crossreactivity with human HBcAg and no crossreactivity with duck HBcAg. Likewise, human HBcAg antibody displays extensive crossreactivity with woodchuck HBcAg and no crossreactivity with duck HbcAg (FIG. 11A).

Example 7

Disassembly and Reassembly of Duck HBcAg Particles

Figure 12:
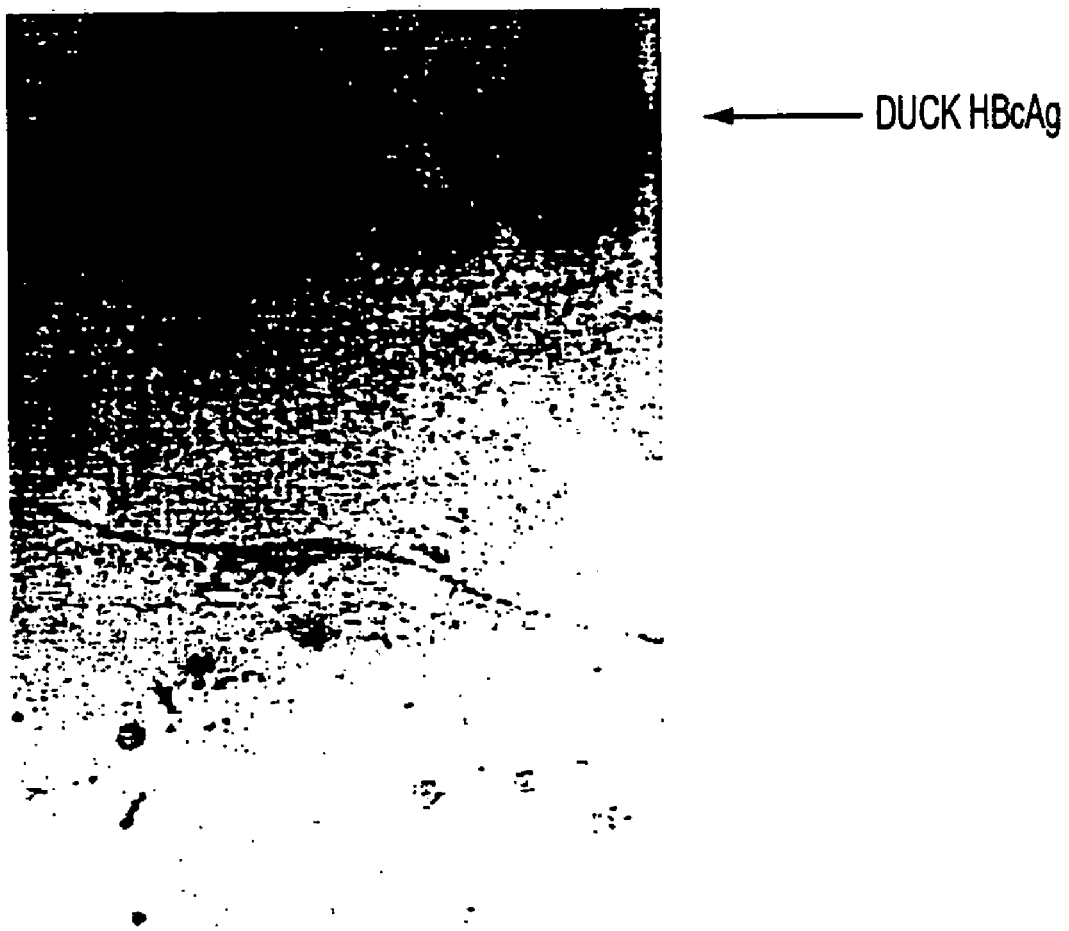
FIG. 12. Disassembly/reassembly of duck HBcAg particle with and without nucleic acids. Lane 1: duck HBcAg; Lane 2: duck HBcAg treated with $MgCl_2$ and dialysed vs. TBS; Lane 3: duck HBcAg treated with both $MgCl_2$ and Rnase A and dialysed; Lane 4: duck HBcAg treated with Rnase A and dialysed.

Experiments were conducted in order to show that the duck HBcAg particles could be successfully disassembled and reassembled. Duck HBcAg (1 mg/mL) was incubated at 37° C. with 0.3 M $MgCl_2$, 7.4 ug/mL Rnase A, or both. After 30 minutes each sample was dialyzed against Tris buffered saline (TBS) for 4 hours and analyzed by native agarose electrophoresis. Treatment with magnesium and subsequent dialysis resulted in reassembly of the treated protein into particles that co-migrated (FIG. 12, lane 2) with the duck HBcAg standard (FIG. 12, lane 1). Treatment with Rnase A alone did not alter the electrophoretic mobility of duck HBcAg (FIG. 12, lane 4), suggesting that Rnase A alone has no apparent effect on the duck HBcAg particle. However, treatment with both Rnase A and $MgCl_2$ results in quantitative removal of a band co-migrating with the duck HBcAg standard (FIG. 12, lane 3). This suggests that in presence of the divalent cation Rnase A can catalyse the hydrolysis of the ribonucleic acid in the particle, i.e. the particle is disassembled, and that nucleic acid is required for the reassembly of the disassociated duck HBcAg. Similar experiments were conducted in which Rnase A/$MgCl_2$ treated duck HBcAg were supplemented with exogenous DNA and tRNA during the dialysis step. No reassembled particles were detected by these methods.

Example 8

Disassembly and Reassembly of Duck HBcAg(1-239) Particles

Figure 13:
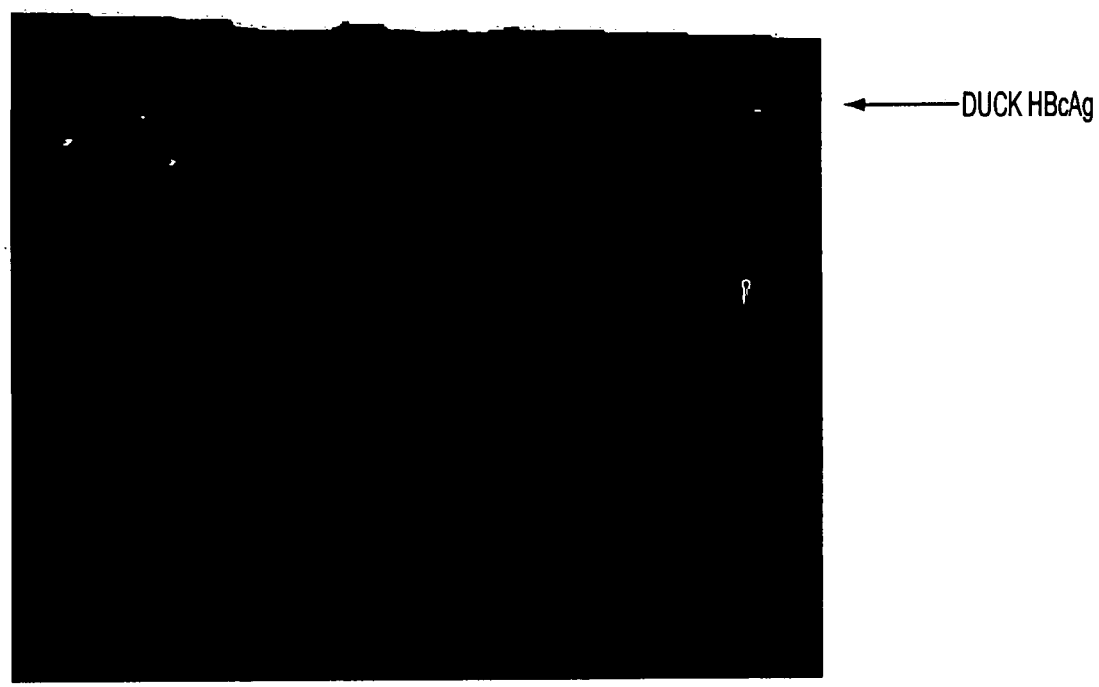
FIG. 13. Disassembly/reassembly of duck HBcAg(1-239) particle with and without nucleic acids. Lane 1: duck HBcAg(1-239); Lane 2: duck HBcAg(1-239) treated with $MgCl_2$ and dialysed vs. TBS; Lane 3: duck HBcAg(1-239) treated with $MgCl_2$ but not dialysed; Lane 4: duck HBcAg (1-239) treated with Rnase A and dialysed; Lane 5: duck HBcAg(1-239) treated with both $MgCl_2$ and Rnase A and dialysed.

Duck HBcAg (1-239) was analyzed by the same method described in Example 7. Identical results were obtained and are given in FIG. 13. Treatment with magnesium and subsequent dialysis resulted in reassembly of the treated protein into particles that co-migrated (FIG. 13, lane 2) with the duck HBcAg(1-239) standard (FIG. 13, lane 1). Treatment with Rnase A alone did not alter the electrophoretic mobility of duck HBcAg(1-239) (FIG. 13, lane 4), suggesting that Rnase A alone has no apparent effect on the duck HBcAg(1-239) particle. However, treatment with both Rnase A and $MgCl_2$ results in quantitative removal of a band co-migrating with the duck HBcAg(1-239) standard (FIG. 13, lane 3). This suggests that in the presence of the divalent cation Rnase A can catalyse the hydrolysis of the ribonucleic acid in the particle, i.e. the particle is disassembled, and that nucleic acid is required for reassembly.

Figure 14:
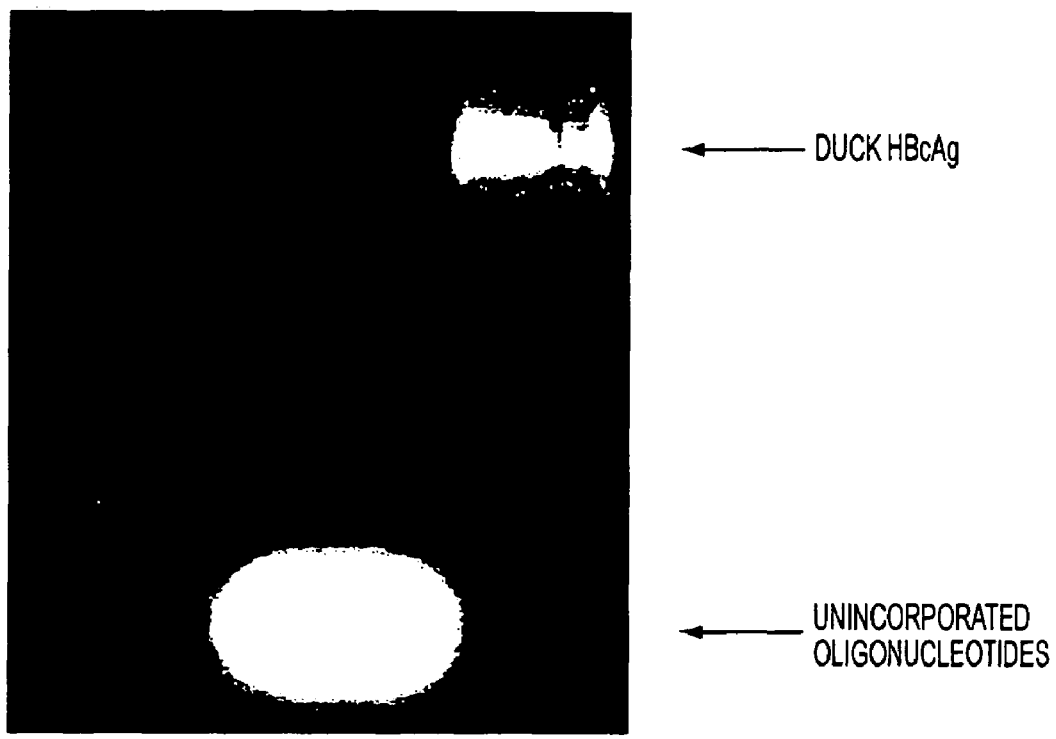
FIG. 14. Disassembly/reassembly of duck HBcAg(1-239) particle with and without nucleic acids. Lane 1: duck HBcAg(1-239) treated with both Rnase A and $MgCl_2$ and dialysed vs. TBS; Lane 2: duck HBcAg(1-239) treated with both Rnase A and $MgCl_2$ and dialysed vs. TBS; exogenous oligonucleotides were added prior to dialysis; Lane 3: duck HBcAg(1-239).
Figure 15:
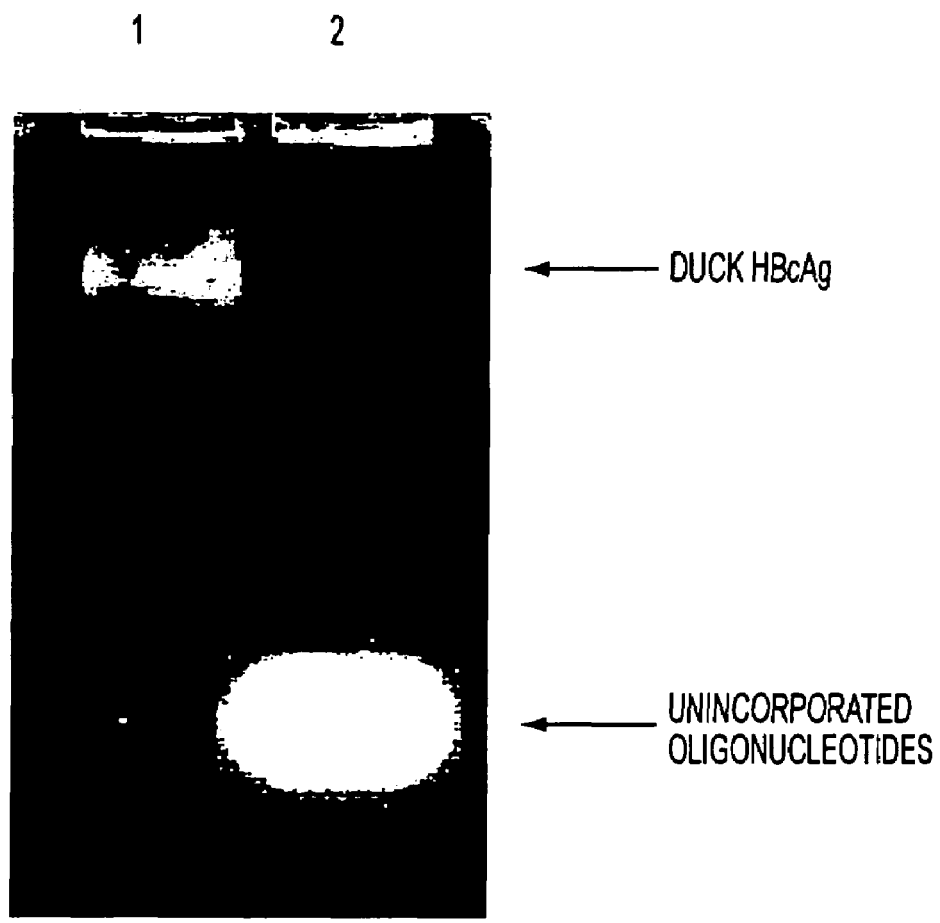
FIG. 15. Disassembly/reassembly of duck HBcAg(1-239) particle with and without nucleic acids. Lane 1: duck HBcAg(1-239); Lane 2: duck HBcAg(1-239) treated with both Rnase A and $MgCl_2$ and dialysed vs. TBS; exogenous oligonucleotides were added prior to dialysis.

However, in contrast to results obtained with full length duck HBcAg, the addition of exogenous DNA to Rnase A/MgCl$_2$ treated duck HBcAg(1-239) supports re-assembly of dissociated monomers into nucleic acid containing core structures. This is illustrated in FIGS. 14 and 15. FIG. 14, Lane 1 shows duck HBcAg(1-239) which has been treated with both Rnase A and MgCl$_2$ and dialysed vs. TBS. FIG. 14, Lane 2 shows duck HBcAg(1-239) which has been treated with both Rnase A and MgCl$_2$ and dialysed vs. TBS and to which exogenous oligonucleotides were added prior to dialysis. As can be seen, a band migrating at the position of control duck HbcAg(1-239) (lane 3) can be seen, indicating particle reassembly in the presence of exogenous oligonucleotides. These results are further illustrated in FIG. 15. Lane 1 of FIG. 15 shows control duck HbcAg(1-239). Lane 2 of FIG. 15 shows duck HbcAg(1-239) which has been treated with both Rnase A and MgCl$_2$ and dialysed vs. TBS, and to which exogenous oligonucleotides were added prior to dialysis. As can be seen, a band migrating at the position of control duck HbcAg(1-239) (lane 1) can be seen, indicating particle reassembly in the presence of exogenous oligonucleotides.

Example 9

Figure 16A:
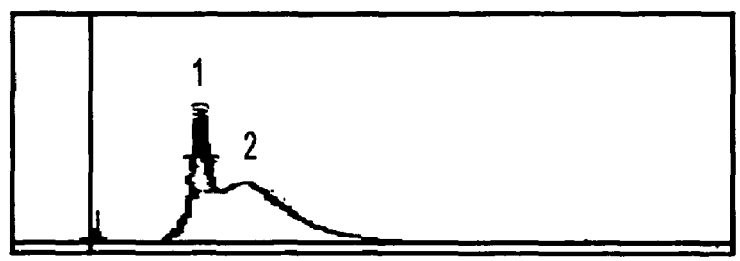
FIGS. 16A, 16B and 16C. Disassembly/reassembly of duck HBcAg(1-239) particle with exogenous nucleic acid: confirmation by chromatography. 16A: Peak 1: breakthrough material representing large molecular weight bacterial aggregates; Peak 2: Duck HBcAg native core peak. 16B: Peak 3: disassociated core monomers; Peak 4: exogenous DNA. 16C: Peak 5: Re-associated duck HBcAg core particles; Peak 6 unincorporated exogenous DNA.
Figure 16B:
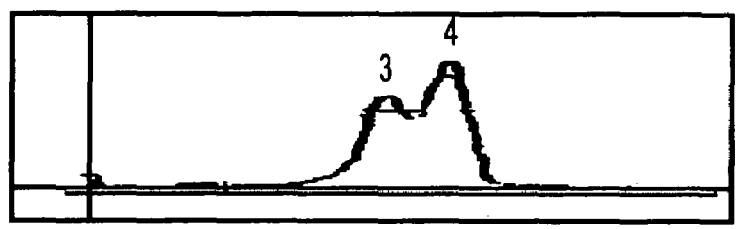
Figure 16C:
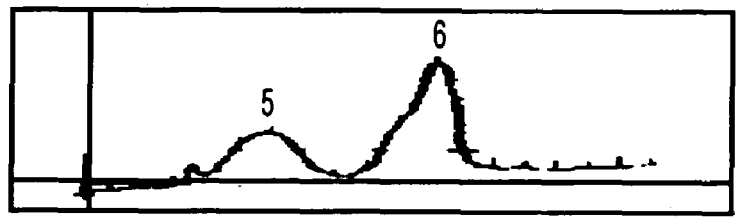

Re-assembly of duck HBcAg(1-239) with exogenous nucleic acid was confirmed by chromatography on Sepharose 4B. The results are shown in FIG. 16, where peak 2 of 16A represents duck HBcAg(1-239) native core peak. (Peak 1 is breakthrough material representing large molecular weight bacterial aggregates). Peak 3 of 16B corresponds to disassociated core monomers (after exposure to divalent cations) and Peak 4 is exogenous DNA. Peak 5 of 16C corresponds to duck HBcAg (1-239) core particles which have reassociated after removal of divalent cations and addition of exogenous DNA; peak 6 represents unincorporated exogenous DNA.

REFERENCES

Beaucage, S. L. and Caruthers, M. R. *Tet. Let.* 21:1859. 1981.

Bringas, R. *J. Structural Biol.* 118:189-196. 1997.

Boggs, R. T. et al., *Antisense and Nuc. Acid Drug Dev.* 1:461-71.1997.

Carson, D. and Raz, E. Oligonucleotide adjuvants to T helper 1 (Th1)-specific vaccinations. *Journal of Experimental Medicine* 186(10), 1621-1622.1997.

Cookson and Moffatt, *Science* 275:4142. 1997.

Davis, H., Weeranta, R., Waldschmidt, T., Tygrett, L., Schorr, J., and Krieg, A. M. CpG DNA is a potent enhancer of specific immunity in mice immunized with recombinant hepatitis B surface antigen. *The Journal of Immunology* 160, 870-876. 1998.

Gaffney, et al., *Tet. Let.* 29: 2619-2622. 1988.

Garegg et al., *Tet. Let.* 27: 4051-4054. 1986.

Goodchild, J. *Bioconjugate Chem.* 1:165. 1990.

Griffiths, J., Harris, S., Layton, G., Berrie, L., French, T., Burns, N., and Kingsman, A., Journal of Virology, 1993, (67) 3191

Harris, S., Gearing, G., Layton, S., and Kingsman. A., Immunology, 1992, (77) 315

Krieg, A. M., Yi, A., Matoson, S., Waldschmidt, T., Bishop, G., Teasdale, R., Koretzky, G., and Klinman, D. CpG motifs in bacterial DNA trigger direct B-cell activation. *Nature* 374, 546-549. 1995.

Krieg, A. M. et al., *Antisense and Nucl. Acid Drug Dev.* 10: 133-9. 1996.

Lipford, G. B., Bauer, M., Blank, C., Reiter, R., Wagner, H., and Heeg, K. CpG-containing sythetic oligonucleotides promote B and cytotoxic responces to protein antigen: a new class of vaccine adjuvants. *European Journal of Immunology* 27, 2340-2344. 1997.

Lipford, G. B., Sparwasser, T., Bauer, M., Zimmermann, S., Koch, E., Heeg, K., and Wagner, H. Immunostimulating DNA: sequence-dependent production of potentially harmful or useful cytokines. European Journal of Immunology 27, 3420-3426. 1997.

Milich, D R., Seminars in Immunology, 1990, (2) 307-315

Milich, D R, Peterson, D L, Zheng, J, Hughes, J, Wirtz, R, and Schodel, F., Annals of the New York Academy of Science, 1995, (754) 187-201

Pisetsky, D. S. Immune activation by bacterial DNA: a new genetic code. *Immunity* 5, 303-310.1996.

Raychaudhuri, S. and Rock, K., Nature Biotechnology, 1998, (16) 1025-1031

Schirmbeck, R. et al. *J. Immunology* 152:1110-1119.1994.

Schirmbeck, R., Bohm, W., Melber, K., and Reimann, J., The Journal of Immunology, 1995, (155) 4676-4684

Schodel, F, Peterson, D L, Hughes, J, and Milich. D., International Review of Immunology, 1994, (ii) 153-165

Schodel, F, Peterson, D L, Hughes, J, and Milich, D R., Journal of Immunology, 1992, (66) 106-114

Schodel, F, Peterson, D L, Zheng, J, Jones, J E, Hughes, J C, and Milich, D R., Vaccine, 1993, (11) 143-148

Sparwasser, T., Koch, E., Vabulas, R., Heeg, K., Lipford, G. B. Ellwart, J., and Wagner, H. Bacterial DNA and immunostimulatory CpG oligonucleotides trigger maturation and ectivation of murine dendritic cells. *European Journal of Immunology* 28, 2045-2054. 1998.

Sparwasser, T., Miethke, T., Lipford, G. B., Erdmann, A., Hacker, H., Heeg, K., and Wagner, H. Macrophages sense pathogens via DNA motifs: induction of tumor necrosis factor-a-mediated shock. *European Journal of Immunology* 27, 1671-1679.1997.

Stacey, K., Sweet, M., and Hume, D. Macrophages ingest and are activated by bacterial DNA. *The Journal of Immunology* 157, 2116-2122. 1996.

Sun, S., Kishimoto, H., and Sprent, J. DNA as an Adjuvant: Capacity of insect DNA and synthetic oligonucleotides to augment T cell responce to specific antigen. *Journal of Experimental Medicine* 187(7), 1145-1150. 1998.

Uhlmann, E. and Peyman, A. *Chem. Rev.* 90:544. 1990.

Wynne, S. A., Crowther, R. A. and Leslie, G. W. *Molecular Cell* 3:771-780. 1999.

Zimmermann, S., Egeter, O., Hausmann, S., Lipford, G. B., Rocken, M., Wagner, H., and Heeg, K. Cutting edge: CpG oligonucleotides trigger protective and curative Th1 response in lethal murine leishmaniasis. *The Journal of Immunology* 160,3627-3730.1998.

We claim:

1. An immunogenic particle comprising duck hepatitis B monomers, wherein at least one of said duck hepatitis B monomers comprises one or more haptens, wherein at least one of said one or more haptens is a foreign, non-duck hapten, and wherein said duck hepatitis B monomers are derived from a truncated version of duck hepatitis B core protein.

2. The immunogenic particle of claim 1, wherein at least one of said duck hepatitis B monomers comprises one hapten.

3. The immunogenic particle of claim 1, wherein at least one of said duck hepatitis B monomers comprises more than one hapten.

4. The immunogenic particle of claim 1, wherein said truncated version of duck hepatitis B core protein does not contain a nucleic acid binding domain.

5. The immunogenic particle of claim 4, wherein the amino acid sequence of said truncated version of duck hepatitis B core protein comprises SEQ ID NO: 21.

6. The immunogenic particle of claim 1, wherein said immunogenic particle further comprises a nucleic acid.

7. An immunogenic particle comprising duck hepatitis B monomers, wherein at least one of said duck hepatitis B monomers comprises one or more haptens, and wherein said duck hepatitis B monomers are derived from a truncated version of duck hepatitis B core protein, wherein a. at least one of said duck hepatitis B monomers comprises more than one hapten; or
b. said truncated version of duck hepatitis B core protein does not contain a nucleic acid binding domain; or
c. the amino acid sequence of said truncated version of duck hepatitis B core protein comprises SEQ ID NO: 21.

* * * * *